United States Patent
Yang

(10) Patent No.: US 11,559,563 B2
(45) Date of Patent: Jan. 24, 2023

(54) USE OF SOLUBLE PRO(RENIN) RECEPTOR TO TREAT METABOLIC DISORDERS AND RELATED CONDITIONS

(71) Applicant: University of Utah Research Foundation, Salt Lake City, UT (US)

(72) Inventor: Tianxin Yang, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 181 days.

(21) Appl. No.: 16/492,457

(22) PCT Filed: Mar. 14, 2018

(86) PCT No.: PCT/US2018/022446
§ 371 (c)(1),
(2) Date: Sep. 9, 2019

(87) PCT Pub. No.: WO2018/170136
PCT Pub. Date: Sep. 20, 2018

(65) Prior Publication Data
US 2021/0213098 A1    Jul. 15, 2021

Related U.S. Application Data

(60) Provisional application No. 62/471,140, filed on Mar. 14, 2017.

(51) Int. Cl.
*A61K 38/00* (2006.01)
*A61K 38/17* (2006.01)

(52) U.S. Cl.
CPC .................................. *A61K 38/177* (2013.01)

(58) Field of Classification Search
CPC ...................................................... A61K 38/177
See application file for complete search history.

(56) References Cited

U.S. PATENT DOCUMENTS 7,351,743 B1 * 4/2008 Goldin ................. A61K 31/155
514/634
2014/0094409 A1   4/2014 Feng

FOREIGN PATENT DOCUMENTS

| CN | 2018800239305 | 3/2018 |
| EP | 18768539.1 | 3/2018 |
| WO | PCT/US2018/022446 | 3/2018 |
| WO | WO-2018/170136 A1 | 9/2018 |

OTHER PUBLICATIONS

U.S. Appl. No. 62/471,140, filed Mar. 14, 2017, Tianxin Yang.
Lu et al. 'Soluble (pro)renin receptor via beta-catenin enhances urine concentration capability as a target of liver X receptor', Proceedings of the National Academy of Sciences,(2016), vol. 113, pp. E1898-E1906.
Tamargo et al. 'Novel therapeutic targets for the treatment of heart failure', Nature Reviews Drug Discovery, Jun. 24, 2011 (Jun. 24, 2011), vol. 10, pp. 536-555.
Vaisbich et al. 'Nephrogenic Diabetes Insipidus (ND): Clinical, Laboratory and Genetic Characterization of Five Brazilian Patients', Clinics, May 2009, vol. 64, pp. 409-414.
International Search Report and Written Opinion dated Jun. 1, 2018 by the International Searching Authority for International Application No. PCT/US2018/022446, filed on Mar. 14, 2018 and published as WO 2018/170136 on Sep. 20, 2018 (Applicant—University of Utah Research Foundation) (9 Pages).
International Preliminary Report on Patentability was dated Sep. 17, 2019 by the International Searching Authority for International Application No. PCT/US2018/022446, filed on Mar. 14, 2018 and published as WO 2018/170136 on Sep. 20, 2018 (Applicant—University of Utah Research Foundation) (6 Pages).
Office Action dated Mar. 9, 2022 by the Chinese Patent Office for Application No. 2018800239305, which was filed on Mar. 14, 2018, (Applicant—University of Utah Research Foundation) (8 pages) (English Translation).
Lu et al., Soluble (pro)renin receptor via B-catenin enhances urine concentration capability as a target of liver X receptor, National Academy of Sciences, vol. 113, No. 13, Mar. 16, 2016.
Quifang et al., "Function of Angiotensin-Converting Enzyme 2" Chinese Journal of Genrontology, vol. 36, pp. 484-487, Jan. 31, 2016.

* cited by examiner

*Primary Examiner* — Jeanette M Lieb
(74) *Attorney, Agent, or Firm* — Ballard Spahr LLP

(57) ABSTRACT

Disclosed are methods of treating obesity or an obesity-related condition comprising administering an effective amount of soluble (pro)renin receptor (sPRR) to a subject that is obese or having an obesity-related condition. In some instances, obesity-related conditions can be, but are not limited to, steatosis, hyperglycemia, insulin resistance, chronic renal disease. Disclosed are methods of reducing body weight comprising administering an effective amount of sPRR to a subject in need thereof. Disclosed are methods of treating fatty liver in a subject comprising administering an effective amount of sPRR to a subject in need thereof. Disclosed are methods of treating a fluid and electrolyte disorder comprising administering an effective amount of sPRR to a subject diagnosed with a fluid and electrolyte disorder.

13 Claims, 18 Drawing Sheets

Specification includes a Sequence Listing.

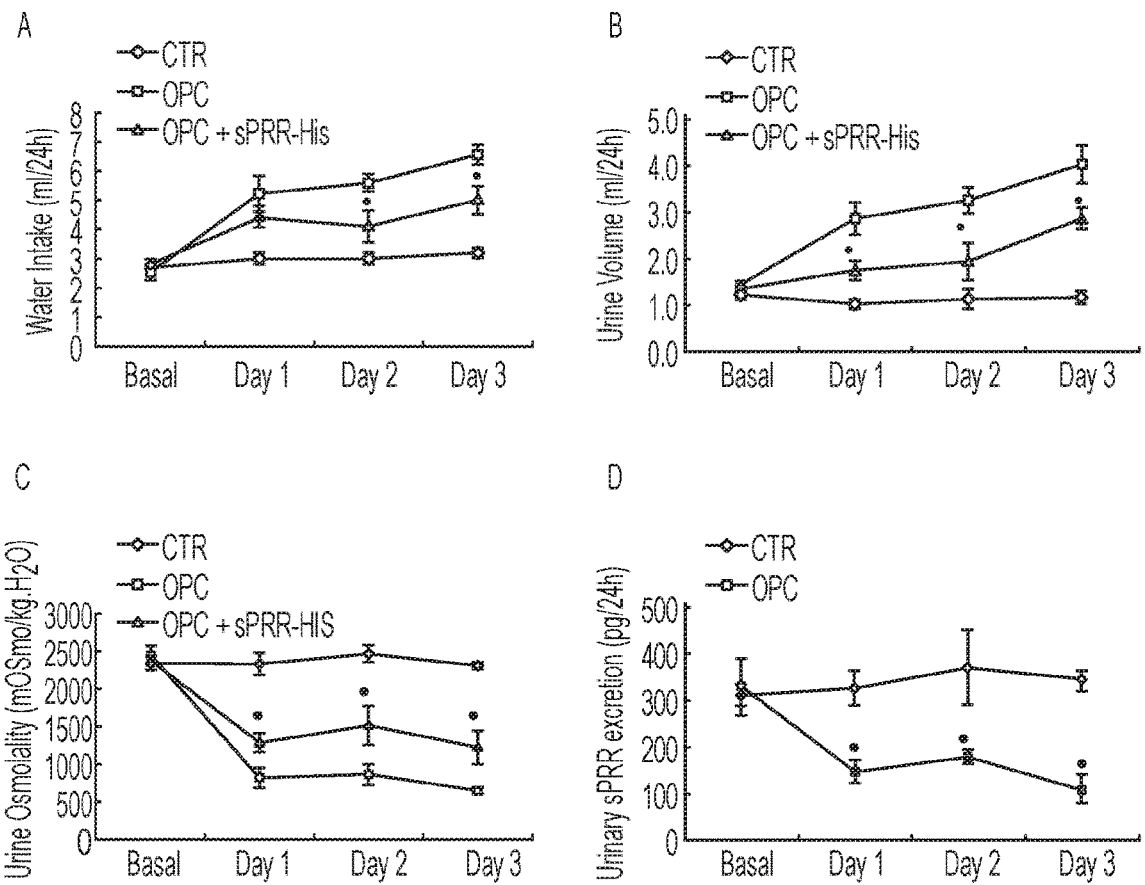
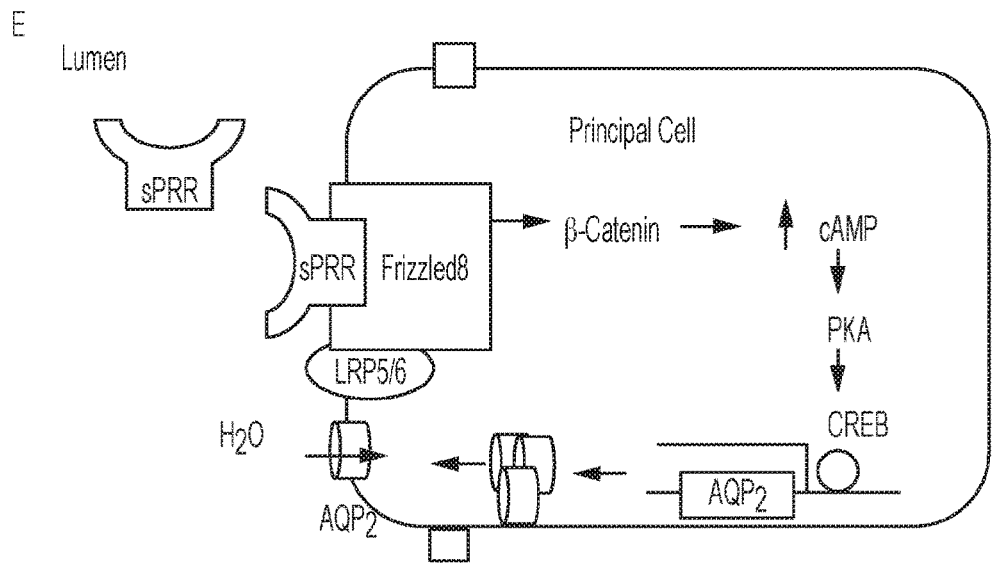
FIG. 8A, FIG. 8B, FIG. 8C, FIG. 8D, FIG. 8E

USE OF SOLUBLE PRO(RENIN) RECEPTOR TO TREAT METABOLIC DISORDERS AND RELATED CONDITIONS

CROSS-REFERENCE TO RELATED APPLICATIONS

The present application is a national phase filing under 35 U.S.C. § 371 of International Application No. PCT/US2018/022446, filed on Mar. 14, 2018, which claims priority to and the benefit of U.S. Provisional Patent Application No. 62/471,140, filed Mar. 14, 2017, which are hereby incorporated by reference in their entirety.

STATEMENT REGARDING FEDERALLY SPONSORED RESEARCH

This invention was made with government support under DK094956 and DK104072 awarded by National Institutes of Health. The government has certain rights in the invention.

BACKGROUND

Reference to Sequence Listing

The Sequence Listing submitted Sep. 9, 2019 as a text file named "21101_0344U2_Sequence_Listing.txt," created on Sep. 9, 2019, and having a size of 2632 bytes is hereby incorporated by reference pursuant to 37 C.F.R. § 1.52(e)(5).

The prevalence of overweight and obese persons has dramatically increased during the past two decades. Currently, 65% of adults in the United States are overweight and 31% of adults are obese. Obesity represents a major risk factor for type 2 diabetes, steatosis, chronic kidney disease, and other chronic diseases. As a result, 18 million Americans are living with diabetes and every minute another American is diagnosed with this disease. The therapies available or management of obesity and obesity-related conditions are limited. In particular, most of these therapies are directed toward individual components of the metabolic syndrome. It is highly desirable to develop a novel therapy to target all or most of the key components of this disease. Thiazolidinediones (TZDs), e.g., rosiglitazone and pioglitazone, are synthetic PPARγ activators which are highly effective for the control of hyperglycemia due to their insulin sensitizing action but have limited beneficial effects on lipid profiles and even deteriorate obesity. TZDs are associated with several major side effects such as edema, body weight gains, and an increased incidence of chronic heart failure. What is needed in an intervention with a wide coverage of multiple components of metabolic syndrome including obesity, hyperglycemia, steatosis, and chronic kidney disease

BRIEF SUMMARY

Full-length (Pro)renin receptor (PRR), is a 350-amino acid transmembrane receptor for prorenin and renin, that can be subjected to protease-mediated cleavage to produce a 28-kDa protein of the N-terminal extracellular domain, the soluble (pro)renin receptor (sPRR), and the 8.9-kDa C-terminal intracellular domain called "M8.9". Described herein is a sPRR based intervention with a wide coverage of multiple components of metabolic syndrome including obesity, hyperglycemia, steatosis, and chronic kidney disease.

Disclosed herein are methods of treating obesity or an obesity-related condition comprising administering an effective amount of soluble (pro)renin receptor (sPRR) to a subject that is obese or having an obesity-related condition. In some instances, obesity-related conditions can be, but are not limited to, steatosis, hyperglycemia, insulin resistance, chronic renal disease.

Disclosed herein are methods of reducing body weight comprising administering an effective amount of sPRR to a subject in need thereof.

Disclosed herein are methods of treating fatly liver in a subject comprising administering an effective amount of sPRR to a subject in need thereof.

Disclosed herein are methods of treating a fluid and electrolyte disorder comprising administering an effective amount of sPRR to a subject diagnosed with a fluid and electrolyte disorder.

Disclosed herein are methods of treating a metabolic disorder comprising administering an effective amount of sPRR to a subject diagnosed with a metabolic disorder.

In some instances, sPRR can be a fusion protein. In some instances, the sPRR can be wild type sPRR. In some instances, sPRR is 70-99% identical to wild type sPRR.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

Figures 1A, 1B, 1C, 1D, 1E, 1F, 1G, 1H, 1I, 1J, 1K, 1L, 1M:
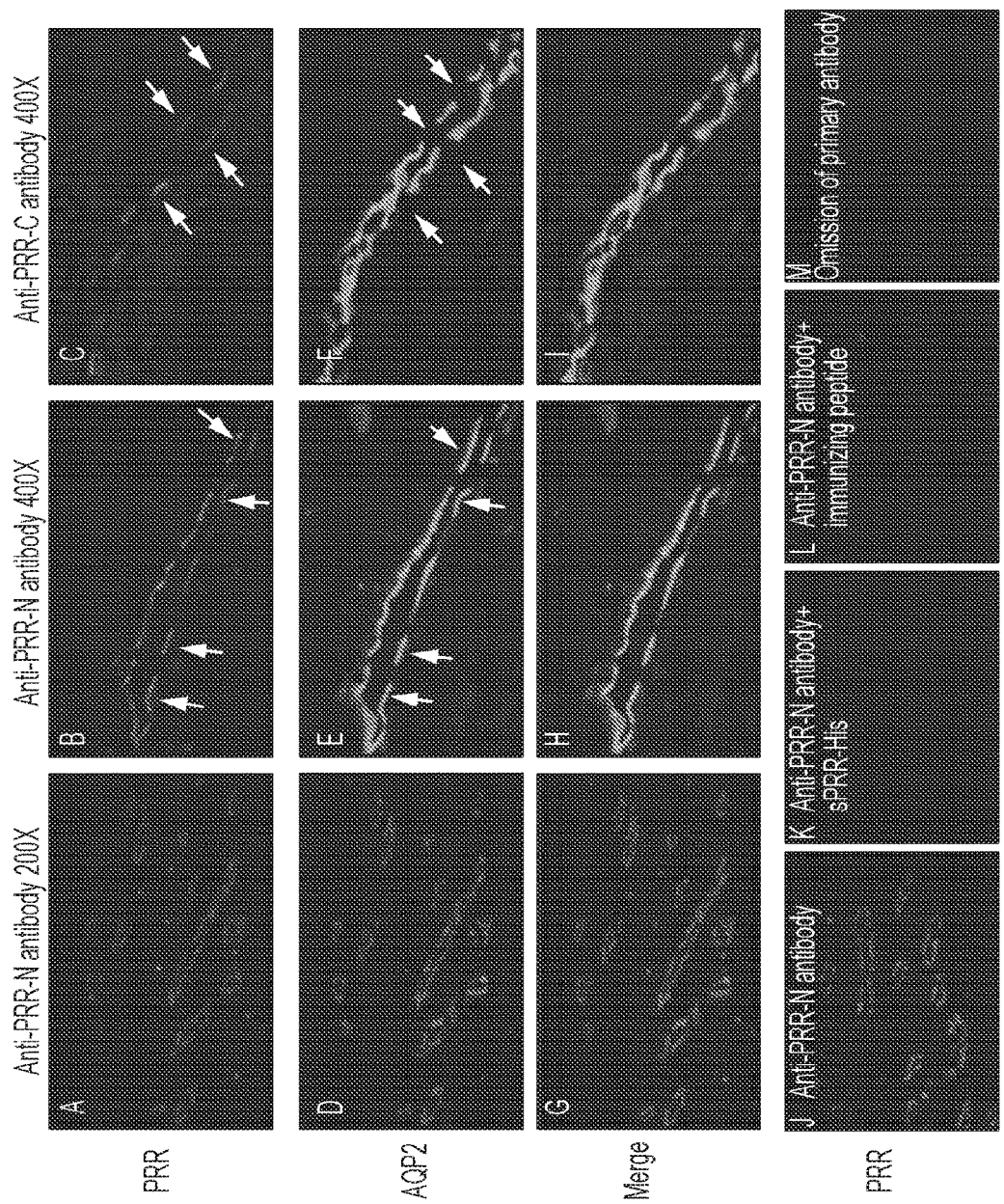
FIGS. 1A-1M show distinct labeling with antibodies against different domains of PRR. (A-C) Immunostaining on consecutive rat kidney sections using anti-PRR-N antibody (magnification: 200× in A: 400× in B) recognizing the N-terminal domain of PRR (e.g., the sPRR sequence) and the anti-PRR-C antibody recognizing the C-terminal domain of PRR (C: magnification: 400×). (D-F) The PRR antibodies were coincubated with anti-AQP2 antibody. (G-I) Merged images. Arrows in B and E denote principal cells; arrows in C and F denote intercalated cells. The labeling with anti-PRR-N antibody was localized mostly to the apical membrane of principal cells, contrasting with the labeling with anti-PRR-C antibody in the intercalated cells. (J-M) To validate the specificity of the labeling, immunostaining was performed with anti-PRR-N antibody preincubated with an expressed sPRR (J), sPRR-His (K), or its immunizing peptides (L) or without the primary antibody (M). The images shown are representative of three to six animals per group.

FIGS. 3A-3D shows renal FZD8 expression and its interaction with sPRR. (A) coimmunoprecipitation analysis of the interaction between sPRR and FZD8. The membrane fraction of rat renal medulla was immunoprecipitated with anti-PRR-N antibody and probed with anti-FZD8 antibody or vice versa. (B) Immunolabeling of FZD8 in rat kidney at low magnification. (C) Immunolabeling of FDZ8, AQP2, and NKCC2 in the outer medulla at high magnification. Colabeling for AQP2 was performed on the same section, and labeling for NKCC2 was performed on consecutive sections. CD, collecting duct; PT, proximal tubule: TL, thick ascending limb. (D) Immunolabeling of FDZ8 and PRR in the rat inner medulla. The consecutive sections were stained with anti-FZD8 antibody and anti-PRR-N antibody. The same section was colabeled with anti-AQP2 antibody. The images shown are representative of three to six animals per group.

FIGS. 4A-4E show an analysis of the in vitro role of the Wnt/β-catenin pathway in the regulation of AQP2 expression in response to sPRR-His treatment. (A) Validation of FZD8 knockdown by siRNA (n=3 per group). Primary rat IMCD cells were transfected with or without FZD8 siRNA. FZD8 protein expression was evaluated by immunoblotting. (B) Effect of sPRR-His on Wnt-response luciferase activity in the presence or absence of FZD8 siRNA (n=12 per group). The IMCD cells were transfected with or without FZD8 siRNA, followed by sPRR-His treatment at 10 nM for 24 h. The Cignal reporter system was used to evaluate the activity of the Wnt/β-catenin pathway, and the data are presented as relative response ratio. (C-E) Rat IMCD cells were transfected with FZD8 siRNA, pretreated with OMP or XAV-939 for 1 h, and treated with 10 nM sPRR for 24 h. AQP2 protein expression was determined by immunoblotting analysis. Densitometric values are shown underneath the blots. (C) Effect of FZD8 knockdown on sPRR-Induced AQP2 protein expression (n=6 per group). (D) Effect of OMP on sPRR-His-induced AQP2 protein expression (n=6 per group). (E) Effect of XAV on sPRR-His-induced AQP2 expression (n=6 per group). Data are shown as mean±SE; *P<0.05 vs. control; #P<0.05 vs. sPRR-His.

FIGS. 5A-5F show a distinct role of the Wnt/D-catenin pathway in the acute and chronic responses to AVP in primary rat IMCD cells. The IMCD cells were pretreated for 1 h with XAV and were treated for 30 min or 24 h with 10 nM AVP. (A) At 30 min of AVP treatment, the medium was assayed for cAMP using ELISA (n=6 per group). (B and C) Membrane fraction (n=6 per group) (B) and cytosolic fraction (n=6 per group) (C) were subjected to immunoblotting analysis of AQP2. (D-F) At 24 h, medium cAMP was determined (n=6 per group) (D), whole-cell lysates were subjected to immunoblotting analysis of AQP2 (n=6 per group) (E), and total RNA was subjected to quantitative RT-PCR analysis of AQP2 mRNA (n=4 per group) (F). Data are shown as mean±SE; *P<0.05 vs. control; #P<0.05 vs. AVP alone.

FIGS. 6A-6H show a role of the Wnt/β-catenin pathway in urine-concentrating capability in rats. SD Rats were administered vehicle, OMP, or XAV and were placed in metabolic cages for assessment of the state of water metabolism at basal condition (A-C) or after 24-h WD (D-H) (n=5 rats per group). At basal the condition, water intake (A), urine volume (B), and urine osmolality (C) were determined. (D-F) During 24-h WD, urine volume (D), urine osmolality (E), and body-weight (BW) changes (F) were monitored. (G and H) At the end of the experiment plasma osmolality (G) and Hct (H) were measured. *P<0.05 vs. control: #P<0.05 vs. WD alone.

FIGS. 7A-7F show an in vivo role of the Wnt/β-catenin pathway in the regulation of renal AQP2 expression during antidiuresis in rats. (A and B) To assess renal β-catenin activation by WD, the nuclear fraction of renal cortex (n=4 rats per group) (A) and the inner medulla (n=4 rats per group) (B) from control and dehydrated rats were subjected to immunoblotting analysis of β-catenin. (C-F) Immunoblotting analysis of AQP2 expression was performed on the renal cortex and the inner medulla of rats treated with vehicle or WD with (C) or without (D) OMP or with (E) or without (F) XAV (n=5 rats per group). Data are shown as mean±SE; *P<0.05 vs. control; #P<0.05 vs. WD. CO, cortex; IM, inner medulla.

FIGS. 8A-8E show the antidiuretic action of sPRR-His in a mouse model of NDI. Male C57/BL6 mice were infused for 7 d with sPRR-His via a catheter implanted in the jugular vein and then received oral administration of either vehicle or the V2R antagonist OPC31260 (OPC) for 3 d. Mice were placed in metabolic cages for assessment of daily water intake and urine output. (A) daily water intake (n=4 mice per group). (B) Daily urine output (n=4 mice per group). (C) Urine osmolality (n=4 mice per group). (D) Urinary sPRR excretion (n=4 mice per group). Data are shown as mean±SE. In A-C, #P<0.05 vs. OPC alone: in D*P<0.05 vs. control. (E) Schematic illustration of the mechanism of action of sPRR. In the lumen of the distal nephron, sPRR binds FZD8 in a receptor complex on the apical membrane of principal cells, resulting in the activation of β-catenin, which promotes cAMP accumulation, ultimately leading to increased AQP2 transcription and enhanced urine concentration.

FIGS. 9A-9I show an initial characterization of diuretic and PRR-inhibitory actions of TO901317 in vivo and in vitro. Male C57/BL7 mice received oral administration of TO901317 with or without i.v. infusion of sPRR-His for 7 d. The mice receiving vehicle treatment served as a control. At the end of experiment, 24-h urine collection was performed, followed by analysis of urinary sPRR excretion by ELISA and renal PRR expression by immunoblotting. (A) Urine output (n=30 mice per group). (B) Urinary osmolality (n=15 mice per group). (C) Immunoblotting analysis of renal PRR expression (n=15 mice per group). (D) Densitometric analysis of the immunoblot in C. (E) ELISA analysis of urinary sPRR (n=8 mice per group). (F-I) The effect of TO901317 on PRR expression in cultured CD cells. mpkCCD cells were exposed to vehicle or 10 μM TO901317 for 24 h. The cell lysates were subjected to immunoblotting analysis of PRR protein expression, and the medium was assayed for sPRR concentration by using ELISA and normalized by protein content. In a separate experiment, the cells were transfected with a PRR-luciferase construct, allowed to grown to confluence, and then were treated with vehicle or 10 μM TO901317 for 24 h. (F) Immunoblotting analysis of PRR (n=15 per group). (G) Densitometric analysis of the immunoblot in A. (H) ELISA analysis of medium sPRR (n=10 per group). (I) The luciferase assay (n=5 per group).

FIGS. 10A-10E shows an effect of sPRR-His on TO901317-induced DI in mice. Male C57/BL6 mice were treated with vehicle or with TO901317 alone or in combination with sPRR-His for 7 d. (A) Urine output (n=8 mice per group). (B) Water intake (n=8 mice per group). (C) Water balance (n=8 mice per group). (D) Urinary osmolality (n=8 mice per group). (E) Hct (n=8 mice per group).

FIGS. 11A-11E shows an effect of sPRR-His on renal AQP2 expression and urinary renin in TO901317-treated mice. Male C57/BL6 mice were treated with vehicle or with TO901317 alone or in combination with sPRR-His for 7 d. AQP2 expression was analyzed by immunoblotting and immunostaining. Urinary renin activity was determined by measuring AngI generation, and urinary prorenin/renin concentration was determined by ELISA. (A) Immunoblotting analysis of AQP2 expression (n=15 mice per group). (B) Densitometric analysis of the immunoblots in A. (C) Urinary renin activity (n=8 mice per group). (D) Urinary prorenin/renin excretion (n=8 mice per group). (E) Schematic illustration of the mechanism by which the LXR agonist T0091317 (TO) suppresses PRR transcription and induces DI. LXRs bound to T0091317 function as a transitional repressor for the PRR gene, leading to a reduced PRR/sPRR level that decreases AQP2 expression, ultimately causing DI.

Figure 12:
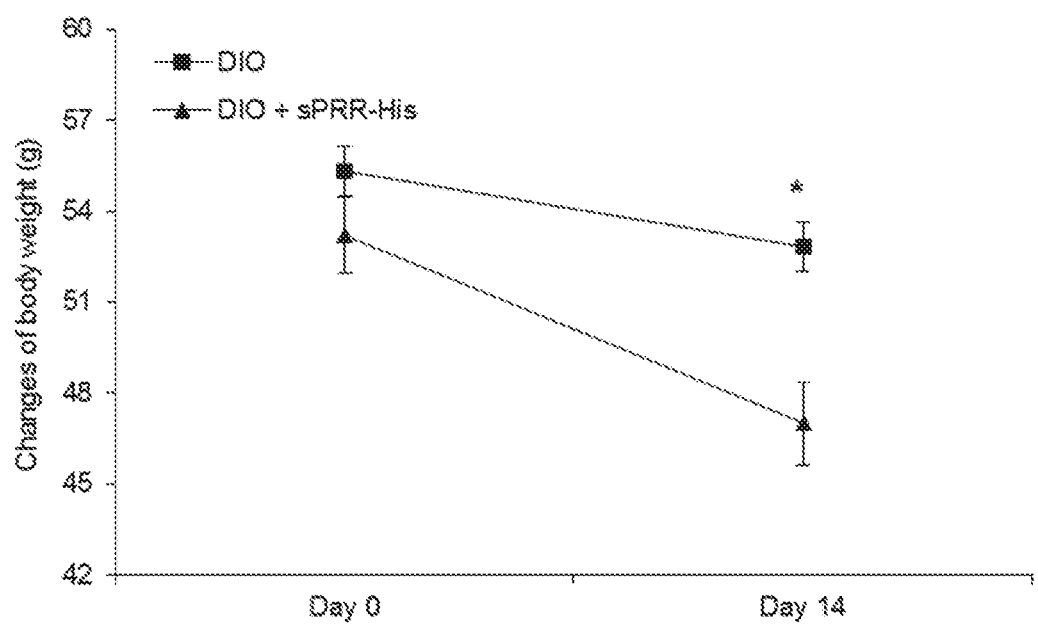

FIG. 12 shows an effect of sPRR-His on body weight in diet-induced obesity in male C57/BL6 mice. Starting from 1 month of age, male C57/BL6 were placed on a high fat diet. During the last 2 wks., mice were randomly divided to receive vehicle or sPRR-His. Shown are body weight changes over the 2-wk treatment period. N=9 per group. Data are mean±SE.

Figure 13:
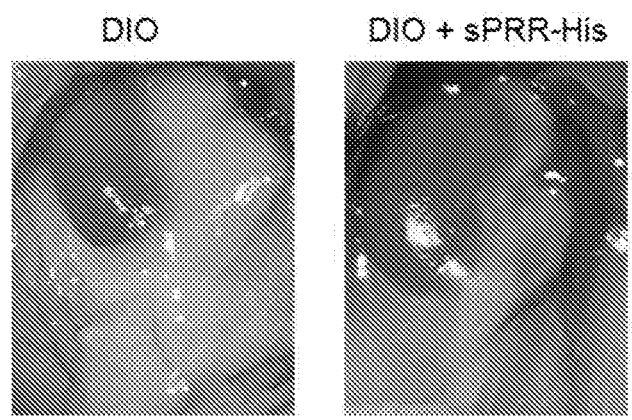

FIG. 13 shows an effect of sPRR-His perirenal fat in DIO mice

Figures 14A, 14B:
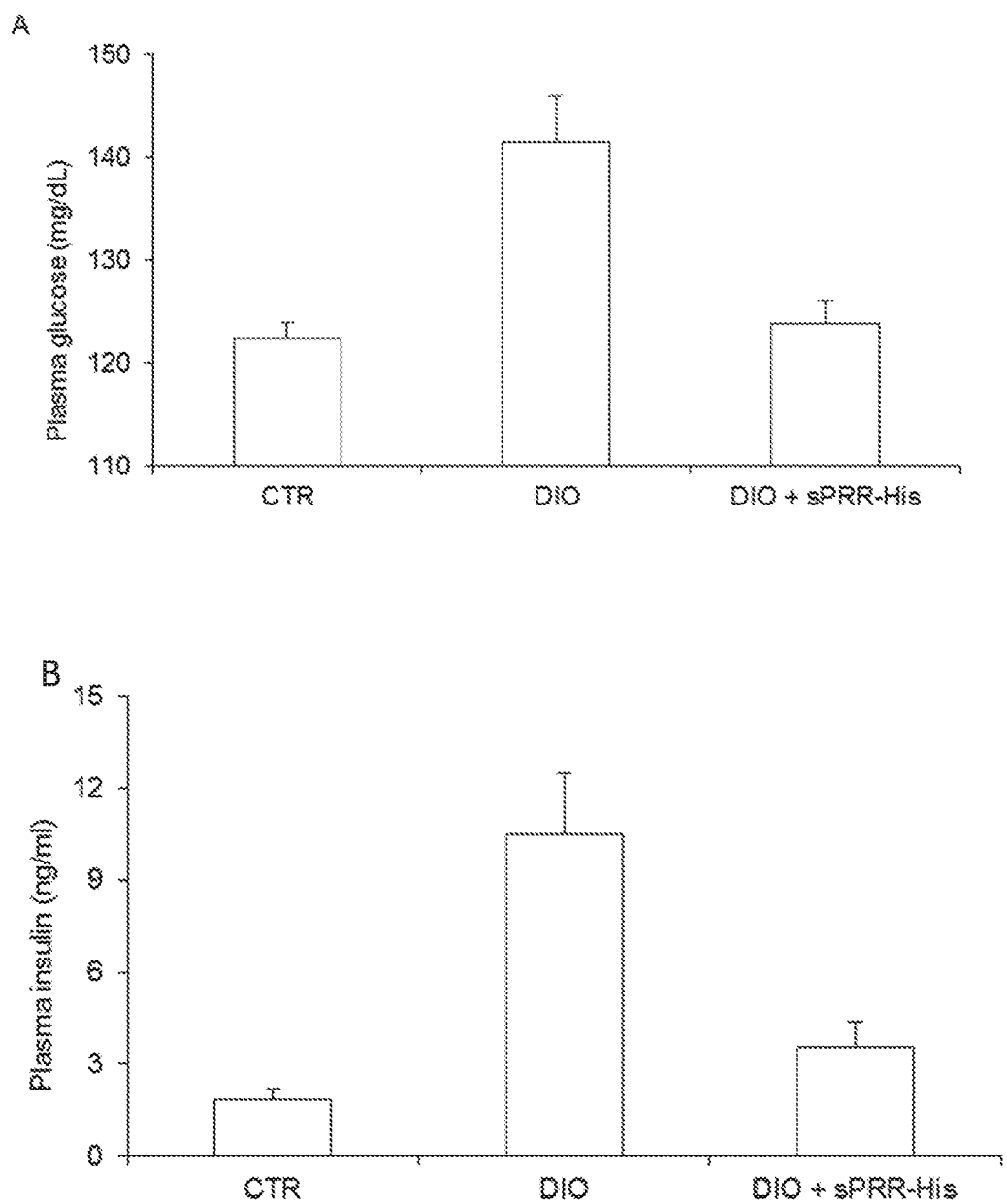

FIGS. 14A and 14B show an effect of sPRR-His on plasma glucose (A) and insulin (B) in DOI mice. Blood glucose was measured by using a glucose meter. Plasma insulin was determined by using EIA. N=9 per group. Data are mean±SE.

Figures 15A, 15B:
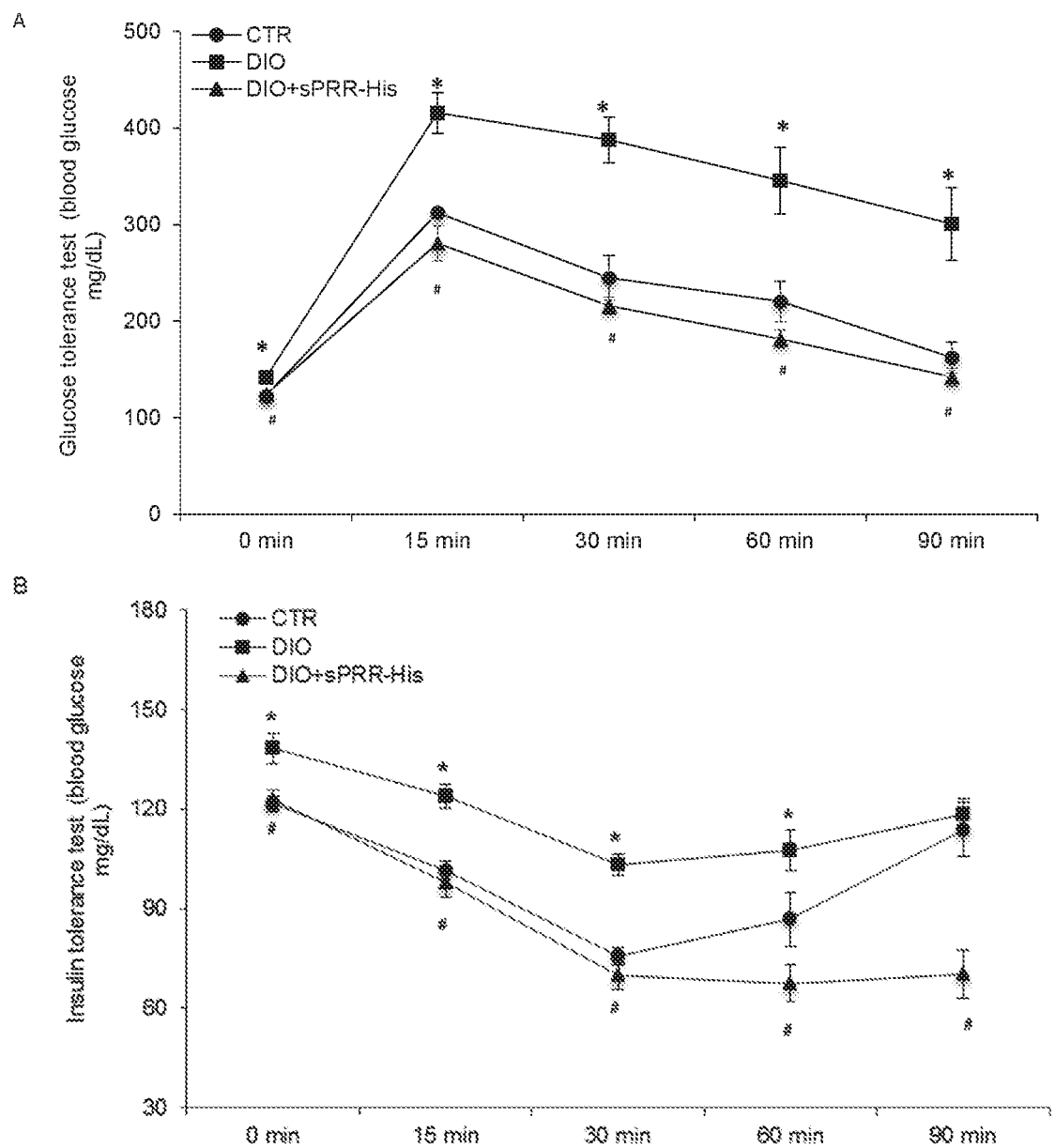

FIGS. 15A and 15B show a glucose tolerance test (GTT) and insulin tolerance test (ITT). After 6 h of fasting, a single dose of glucose or insulin (0.25 U/kg body weight) was administered via IP injection. This was followed by a series of blood collection and measurement of blood glucose. N=9 per group. Data are mean±SE.

Figures 16A, 16B, 16C:
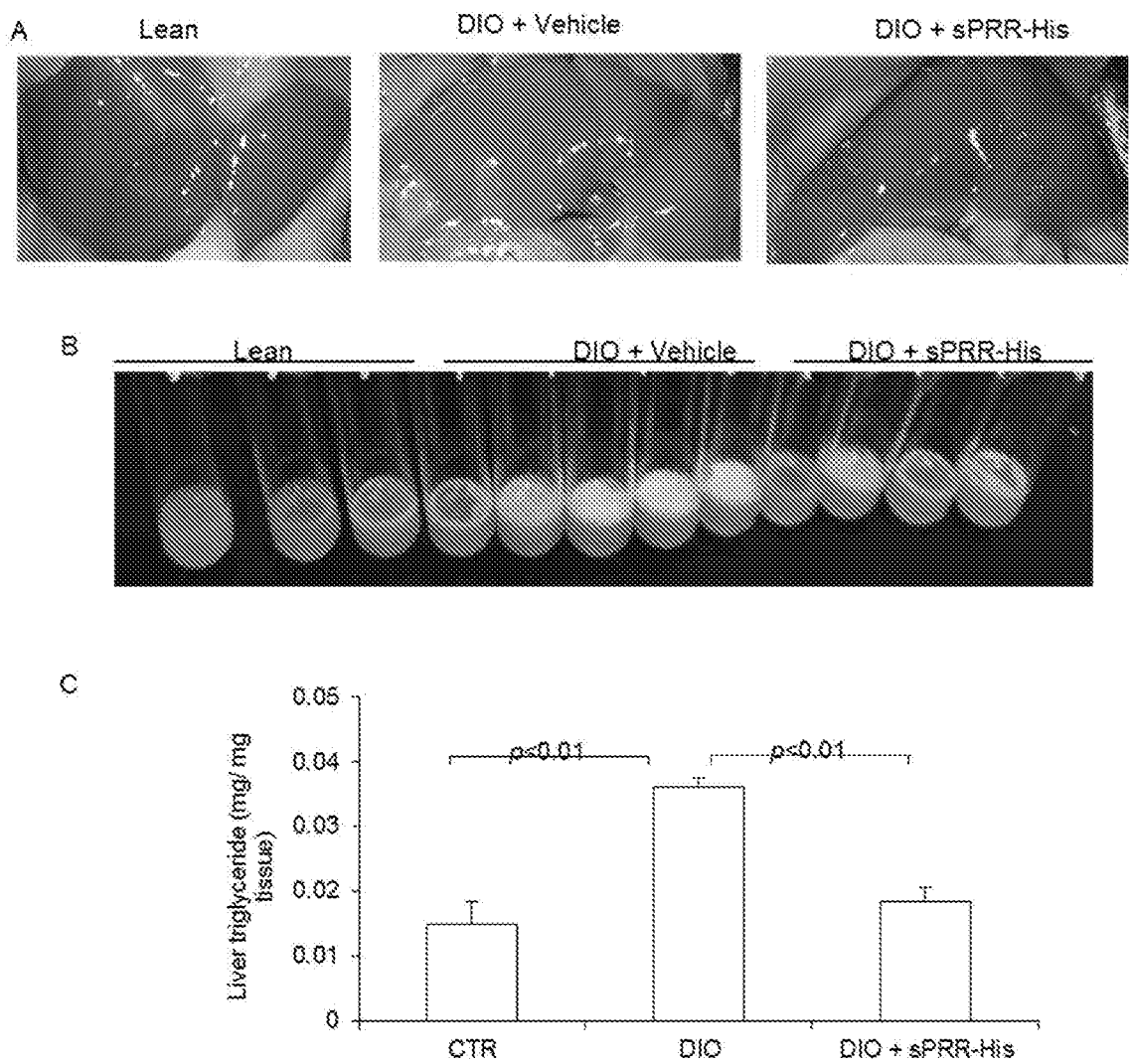

FIGS. 16A-C show an effect of sPRR-His on steatosis in DIO mice. (A) The gross appearance of the liver. Shown is a representative image. (B) the appearance of the lipid layer in liver homogenates after centrifugation. Shown are samples from 4 representative animals per group. (C) Liver triglyceride content. N=9 per group. Data are mean±SE.

Figure 17:
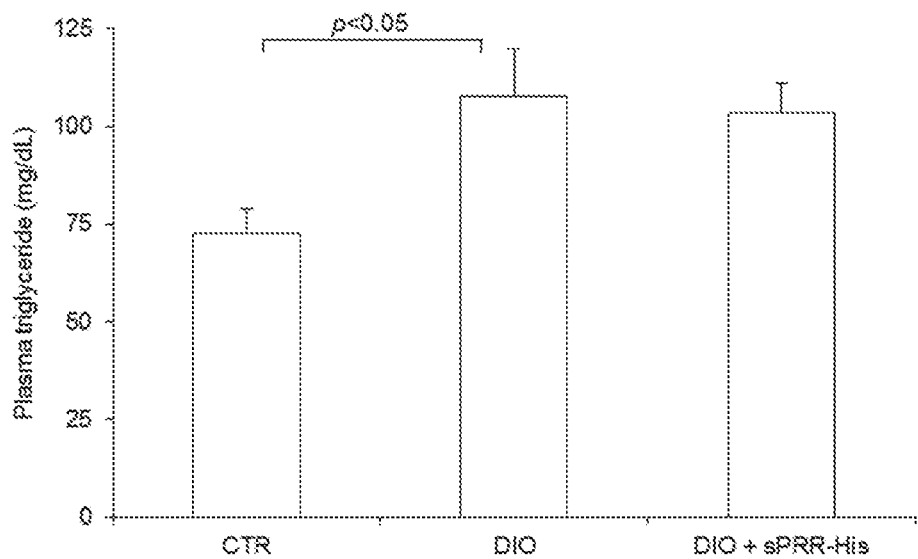

FIG. 17 shows an effect of sPRR-His on plasma triglyceride in DIO mice. N=9 per group. Data are mean±SE.

Figure 18:
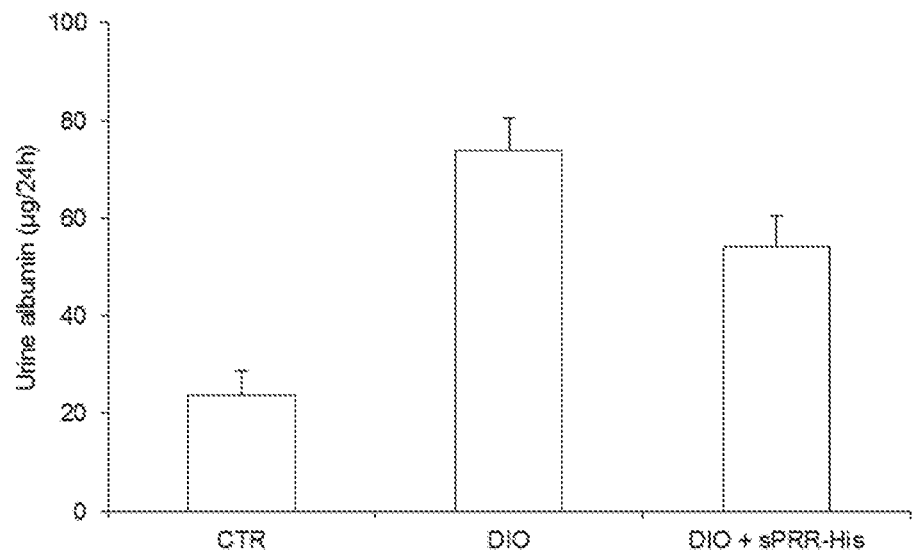

FIG. 18 shows an effect of sPRR-His on albuminuria in DIO mice. Urine albumin was determined by using EIA. N=9 per group. Data are mean±SE.

Figures 19A, 19B:
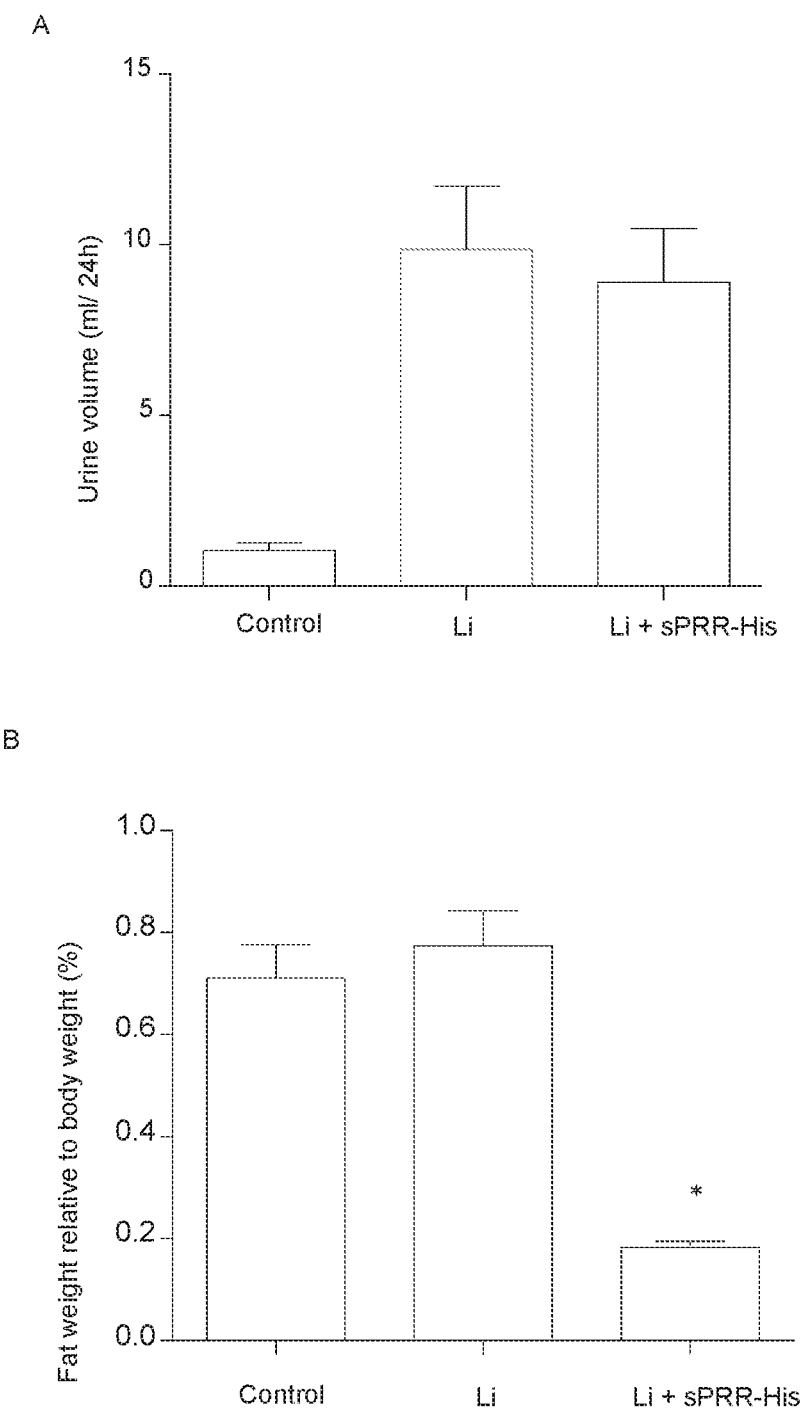
Figure 19C:
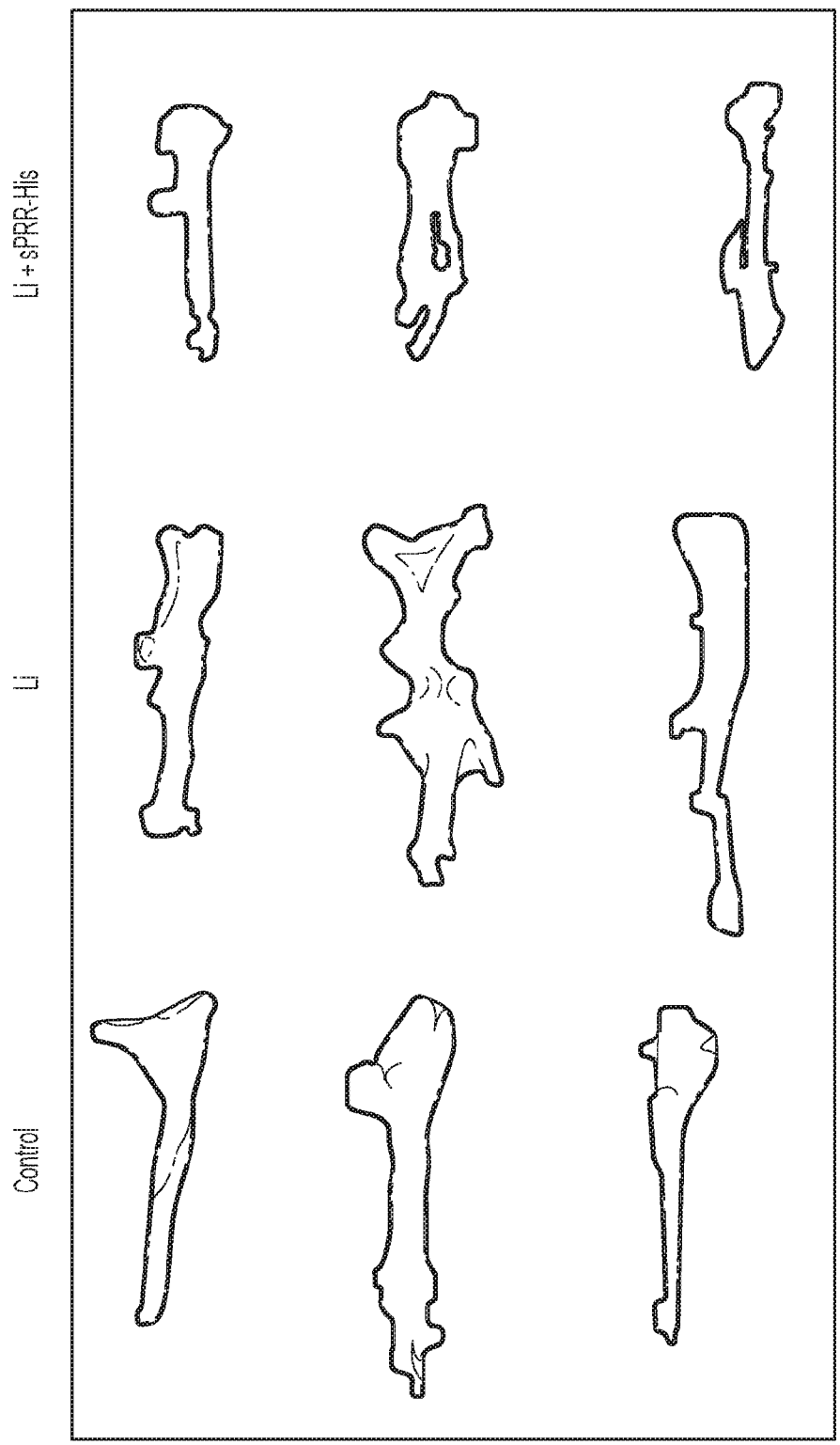

FIGS. 19A, 19B, and 19C show an effect of sPRR-His on urine volume and apididymal fat mass and in lithium-treated mice. Although co-administration with sPRR-His didn't affect Li-induced polyuria (FIG. 19A) but surprisingly reduced fat mass (FIG. 19B). The image of apididymal fat is shown in FIG. 19C. The fat in the Li+sPRR-His group is smaller and also more "browning" than that in the other two groups. N=4-5 per group. Data are mean±SE.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. If a class of molecules A, B. and C are disclosed as well as a class of molecules D, E, and F and an example of a combination molecule. A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C: D, E, and F: and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a sPRR" includes a plurality of such sPRRs, reference to "the sPRR" is a reference to one or more sPRRs and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

As used herein, the term "subject" or "patient" refers to any organism to which a composition of this invention may be administered, e.g., for experimental, diagnostic, and/or therapeutic purposes. Typical subjects include animals (e.g., mammals such as non-human primates, and humans: avians: domestic household or farm animals such as cats, dogs, sheep, goats, cattle, horses and pigs: laboratory animals such as mice, rats and guinea pigs; rabbits; fish; reptiles; zoo and wild animals). Typically, "subjects" are animals, including mammals such as humans and primates; and the like.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "therapeutic" refers to a treatment, therapy, or drug that can treat a disease or condition or that can ameliorate one or more symptoms associated with a disease or condition.

"Effective amount" means the amount of active pharmaceutical agent sufficient to effectuate a desired physiological outcome in an individual in need of the agent. The effective amount can vary among subjects depending on the health and physical condition of the subject to be treated, the taxonomic group of subjects to be treated, the formulation of the sPRR, assessment of the subject's medical condition, and other relevant factors.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the materials for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Methods of Treating Metabolic Disorders and Related Conditions

Disclosed are methods of treating a metabolic disorder comprising administering an effective amount of sPRR to a subject. Disclosed are methods of treating a metabolic disorder comprising administering an effective amount of sPRR to a subject diagnosed with a metabolic disorder. A metabolic disorder can happen when abnormal chemical reactions in the body alter the normal metabolic process. Symptoms of a metabolic disorder can include lethargy, abdominal pain, weight loss, jaundice, and seizures. In some instances, metabolic disorders include, but are not limited to, obesity and obesity-related conditions, fluid and electrolyte disorders, lipid disorders, diabetes mellitus, exercise-associated hyponatremia, metabolic myopathy, pancreatitis, pansteatitis, X-linked hypophosphatemia, and lysosomal storage disorders.

C. Methods of Treating Obesity or Obesity-Related Conditions

Disclosed are methods of treating obesity or an obesity-related condition comprising administering an effective amount of soluble (pro)renin receptor (sPRR) to a subject that is obese or having an obesity-related condition. In some instances, obesity-related conditions can be, but are not limited to, steatosis, hyperglycemia, insulin resistance, chronic renal disease.

Disclosed are methods of treating obesity or an obesity-related condition comprising administering an effective amount of soluble (pro)renin receptor (sPRR) to a subject that is obese or having an obesity-related condition further comprising the step of testing the subject to determine whether the subject is obese or has an obesity-related condition prior to administering the sPRR.

Disclosed are methods of reducing body weight comprising administering an effective amount of sPRR to a subject in need thereof. In some instances, a subject in need thereof is any subject having been diagnosed with needing to lose weight.

Disclosed are methods of treating fatty liver in a subject comprising administering an effective amount of sPRR to a subject in need thereof. In some instances, a subject in need thereof is any subject having been diagnosed with fatty liver. In some instances, fatty liver can be nonalcoholic fatty liver disease (NAFLD) or alcoholic liver disease (ALD).

In some instances, administering an effective amount of sPRR comprises administering a vehicle carrying an effective amount of sPRR. In some instances, the vehicle can be a nanoparticle. For example, the nanoparticle can be a lipsome or polymer. In some instances, the vehicle can have a targeting moiety, wherein the targeting moiety can target the sPRR to a particular cell or tissue of interest.

Disclosed are methods of treating obesity or an obesity-related condition comprising administering an effective amount of sPRR to a subject that is obese or having an obesity-related condition further comprising administering a known therapeutic. In some instances, the known therapeutic is known to treat obesity or an obesity-related condition. For example, known therapeutics for treating obesity or an obesity-related condition can be, but are not limited to, GLP-1 receptor agonists (e.g. Saxenda®). In some instances, the sPRR and the known therapeutic are administered simultaneously. In some instances, the sPRR and the known therapeutic are administered consecutively. In some instances, the sPRR and the known therapeutic are formulated together. In some instances, the sPRR and the known therapeutic are formulated separately.

Disclosed are methods of reducing body weight comprising administering an effective amount of sPRR to a subject in need thereof further comprising administering a known therapeutic. In some instances, the known therapeutic is known to reduce body weight. For example, known therapeutics for reducing body weight can be, but are not limited to, the same therapeutics used to treat obesity. In some instances, the sPRR and the known therapeutic are administered simultaneously. In some instances, the sPRR and the known therapeutic are administered consecutively. In some instances, the sPRR and the known therapeutic are formulated together. In some instances, the sPRR and the known therapeutic are formulated separately.

Disclosed are methods of treating fatty liver in a subject comprising administering an effective amount of sPRR to a subject in need thereof further comprising administering a known therapeutic. In some instances, the known therapeutic is known to treat fatty liver. For example, known therapeutics for treating fatty liver can be, but are not limited to, statins and thiazolidinedione. In some instances, the sPRR and the known therapeutic are administered simultaneously. In some instances, the sPRR and the known therapeutic are administered consecutively. In some instances, the sPRR and the known therapeutic are formulated together. In some instances, the sPRR and the known therapeutic are formulated separately.

In some instances, sPRR can be a fusion protein. For example, the sPRR fusion partner can be, but is not limited to, a histidine (His) tag, a glutathione-S-transferase (GST) tag, a c-Myc tag, hemaglutanin (HA) tag or myelin basic protein (MBP) tag.

In some instances, the sPRR can be wild type sPRR. For example, wild type sPRR can be the sequence of SEQ ID NO:1.

(SEQ ID NO: 1)
ANEFSILRSPGSVVFRNGNWPIPGDRIPDVAALSMGFSVKEDLSWP

GLAVGNLFHRPRATIMVTVKGVDKLALPTGSVISYPLENAVPFSLD

-continued

SVANSIHSLFSEETPVVLQLAPSEERVYMVGKANSVFEDLSVTLRQ

LRNRLFQENSVLNSLPLNSLSRNNEVDLLFLSELQVLHDISSLLSR

HKHLAKDHSPDLYSLELAGLDELGKRYGEDSEQFRDASRILVDALQ

KFADDMYSLYGGNAVVELVTVKSFDTSL

In some instances, sPRR is 70-99% identical to wild type sPRR. In some instances, the substituted amino acids can be modified amino acids, conservative substitutions or non-conservative substitutions.

In some instances, sPRR can be administered in an amount of 10-300 µg/kg/day. In some instances, the dosing regimen can include a single administration of sPRR. In some instances, the dosing regimen can include administering sPRR once a week, twice a week, three times a week, four times a week, five times a week, six times a week, or seven times a week for 1, 2, 3, 4, 5, 6, 7, 8, 9, 10, 11, 12, 13, 14, 15, 16, 17, 18, 19, 20, 21, 22, 23, 24, 26, 28, 30, 32, 34, 36, 38, 40, 42, 44, 46, 48, 50 or 52 weeks.

D. Methods of Treating Fluid and Electrolyte Disorders

Disclosed are methods of treating a fluid and electrolyte disorder comprising administering an effective amount of sPRR to a subject diagnosed with a fluid and electrolyte disorder. In some instances, fluid and electrolyte disorders includes, but are not limited to, central diabetes insipidus (CDI), nephrogenic diabetes insipidus (ND), hemorrhagic shock, septic shock, and plasma volume contraction due to a variety of etiologies.

Disclosed are methods of treating a fluid and electrolyte disorder comprising administering an effective amount of sPRR to a subject diagnosed with a fluid and electrolyte disorder further comprising the step of testing the subject to determine whether the subject has a fluid and electrolyte disorder prior to administering the sPRR In some instances, administering an effective amount of sPRR comprises administering a vehicle carrying an effective amount of sPRR. In some instances, the vehicle can be a nanoparticle. For example, the nanoparticle can be a lipsome or polymer. In some instances, the vehicle can have a targeting moiety, wherein the targeting moiety can target the sPRR to a particular cell or tissue of interest.

Disclosed are methods of treating a fluid and electrolyte disorder comprising administering an effective amount of sPRR to a subject diagnosed with a fluid and electrolyte disorder further comprising administering a known therapeutic. In some instances, the known therapeutic is known to treat fluid and electrolyte disorders. For example, known therapeutics for treating fluid and electrolyte disorders can be, but are not limited to, thiazolidinedione, insulin, metformin, glycodiuretic. In some instances, the sPRR and the known therapeutic are administered simultaneously. In some instances, the sPRR and the known therapeutic are administered consecutively. In some instances, the sPRR and the known therapeutic are formulated together. In some instances, the sPRR and the known therapeutic are formulated separately.

In some instances, sPRR can be a fusion protein. For example, the sPRR fusion partner can be, but is not limited to, a histidine (His) tag, a glutathione-S-transferase (GST) tag, a c-Myc tag, hemaglutanin (HA) tag or myelin basic protein (MBP) tag.

In some instances, the sPRR can be wild type sPRR. For example, wild type sPRR can be the sequence of SEQ ID NO:1.

In some instances, sPRR is 70-99% identical to wild type sPRR. In some instances, the substituted amino acids can be modified amino acids, conservative substitutions or non-conservative substitutions.

In some instances, sPRR can be administered in an amount of 10-300 μg/kg/day. In some instances, the dosing regimen can include a single administration of sPRR. In some instances, the dosing regimen can include administering sPRR once a week, twice a week, three times a week, four times a week, five times a week, six times a week, or seven times a week for 1, 2, 3, 4, 5, 6, 7, 8, 9, 10, 11, 12, 13, 14, 15, 16, 17, 18, 19, 20, 21, 22, 23, 24, 26, 28, 30, 32, 34, 36, 38, 40, 42, 44, 46, 48, 50 or 52 weeks.

E. Compositions and Formulations

Disclosed are compositions comprising a peptide comprising a sPRR

As described hereon, in some instances, the sPRR can be wild type sPRR. For example, wild type sPRR can be the sequence of SEQ ID NO:1. In some instances, sPRR is 70-99% identical to wild type sPRR. In some instances, the substituted amino acids can be modified amino acids, conservative substitutions or non-conservative substitutions.

In some instances, sPRR can be a fusion protein. For example, the sPRR fusion partner can be, but is not limited to, a histidine (His) tag, a glutathione-S-transferase (GST) tag, a c-Myc tag, hemaglutanin (HA) tag or myelin basic protein (MBP) tag.

In some instances, the sPRR can be formulated and/or administered in or with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Thus, the compositions disclosed herein can comprise, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989): Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In one aspect, disclosed are pharmaceutical compositions comprising any of the disclosed peptides described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides, nucleic acids, vectors and/or antibodies described herein can be used to produce a composition which can also include a carrier such as a pharmaceutically acceptable carrier. For example, disclosed are pharmaceutical compositions, comprising the peptides disclosed herein, and a pharmaceutically acceptable carrier. In one aspect, disclosed are pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, disclosed are pharmaceutical composition comprising a pharmaceutically acceptable carrier or diluent and, as active ingredient, a therapeutically effective amount of a disclosed compound, a product of a disclosed method of making, a pharmaceutically acceptable salt, solvate, or polymorph thereof, a hydrate thereof, a solvate thereof, a polymorph thereof, or a stereochemically isomeric form thereof. In a further aspect, a disclosed compound, a product of a disclosed method of making, a pharmaceutically acceptable salt, solvate, or polymorph thereof, a hydrate thereof, a solvate thereof, a polymorph thereof, or a stereochemically isomeric form thereof, or any subgroup or combination thereof may be formulated into various pharmaceutical forms for administration purposes.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline. N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the disclosed compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The disclosed compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. The lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Thus, the pharmaceutical compositions of this invention can include a pharmaceutically acceptable carrier and a compound or a pharmaceutically acceptable salt of the compounds of the invention. By "pharmaceutically acceptable" is meant a material or carrier that would be selected to minimize any degradation of the active ingredient and to minimize any adverse side effects in the subject, as would be well known to one of skill in the art. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other examples of carriers include dimyristoylphosphatidyl (DMPC), phosphate buffered saline or a multivesicular liposome. For example, PG:PC:Cholesterol: peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Because of the ease in administration, oral administration is preferred, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a peptide such as sPRR (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution. Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require positive allosteric modulation of metabotropic glutamate receptor activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration: the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned diseases, disorders or conditions.

It is understood that the disclosed compositions can be prepared from the disclosed compounds. It is also understood that the disclosed compositions can be employed in the disclosed methods of using.

As already mentioned, the invention relates to a pharmaceutical composition comprising a therapeutically effective amount of a disclosed compound, a product of a disclosed method of making, a pharmaceutically acceptable salt, solvate, or polymorph thereof, a hydrate thereof, a solvate thereof, a polymorph thereof, and a pharmaceutically acceptable carrier. Additionally, the invention relates to a process for preparing a pharmaceutical composition, characterized in that a pharmaceutically acceptable carrier is intimately mixed with a therapeutically effective amount of a compound according to the invention.

As already mentioned, the invention also relates to a pharmaceutical composition comprising a disclosed peptide, a pharmaceutically acceptable salt, solvate, or polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present invention also relates to a combination of disclosed peptides, a pharmaceutically acceptable salt, solvate, or polymorph thereof, and an anti-cancer therapeutic agent. In various further aspects, the present invention also relates to a combination of disclosed peptides, a pharmaceutically acceptable salt, solvate, or polymorph thereof. The present invention also relates to such a combination for use as a medicine. The different drugs of such a combination or product may be combined in a single preparation together with pharmaceutically acceptable carriers or diluents, or they may each be present in a separate preparation together with pharmaceutically acceptable carriers or diluents.

In some instances, sPRR can be administered in an amount of 10-300 µg/kg/day. In some instances, the dosing regimen can include a single administration of sPRR. In some instances, the dosing regimen can include administering sPRR once a week, twice a week, three times a week, four times a week, five times a week, six times a week, or seven times a week for 1, 2, 3, 4, 5, 6, 7, 8, 9, 10, 11, 12, 13.14, 15, 16, 17, 18, 19, 20, 21, 22, 23, 24, 26, 28, 30, 32, 34, 36, 38, 40, 42, 44, 46, 48, 50 or 52 weeks.

F. Administering

In the methods described herein, administration or delivery of the sPRR or known therapeutic to a subject can be via a variety of mechanisms. For example, the sPRR or known therapeutic can be formulated as a pharmaceutical composition.

Pharmaceutical compositions can be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution. Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for treating obesity, obesity-related conditions and fluid and electrolyte disorders, the kit comprising sPRR and a vehicle for carrying the sPRR. Disclosed are kits for treating a metabolic disorder, the kit comprising sPRR and a vehicle for carrying the sPRR Examples A. Soluble (Pro)Renin Receptor Via β-Catenin Enhances Urine Concentration Capability as a Target of Liver X Receptor The extracellular domain of the (pro)renin receptor (PRR) is cleaved to produce a soluble (pro)renin receptor (sPRR) that is detected in biological fluid and elevated under certain pathological conditions. The present study was performed to define the antidiuretic action of sPRR and its potential interaction with liver X receptors (LXRs), which are known regulators of urine-concentrating capability. Water deprivation consistently elevated urinary sPRR excretion in mice and humans. A template-based algorithm for protein-protein interaction predicted the interaction between sPRR and frizzled-8 (FZD8), which subsequently was confirmed by coimmunoprecipitation. A recombinant histidine-tagged sPRR (sPRR-His) in the nanomolar range induced a remarkable increase in the abundance of renal aquaporin 2 (AQP2) protein in primary rat inner medullary collecting duct cells. The AQP2 up-regulation relied on sequential activation of FZD8-dependent β-catenin signaling and cAMP-PKA pathways. Inhibition of FZD8 or tankyrase in rats induced polyuria, polydipsia, and hyperosmotic urine. Administration of sPRR-His alleviated the symptoms of diabetes insipidus induced in mice by vasopressin 2 receptor antagonism. Administration of the LXR agonist TO901317 to C57/BL6 mice induced polyuria and suppressed renal AQP2 expression associated with reduced renal PRR expression and urinary sPRR excretion. Administration of sPRR-His reversed most of the effects of TO901317. In cultured collecting duct cells, TO901317 suppressed PRR protein expression, sPRR release, and PRR transcriptional activity. This study demonstrates that sPRR exerts antidiuretic action via FZD8-dependent stimulation of AQP2 expression and that inhibition of this pathway contributes to the pathogenesis of diabetes insipidus induced by LXR agonism.

Full-length (Pro)renin receptor (PRR), a 350-amino acid transmembrane receptor for prorenin and renin, is subjected to protease-mediated cleavage to produce a 28-kDa protein of the N-terminal extracellular domain, the soluble (pro) renin receptor (sPRR), and the 8.9-kDa C-terminal intracellular domain called "M8.9". Before the cloning of full-length PRR in mesangial cells as an integral 39-kDa membrane protein, M8.9 was identified as a truncated protein associated with the vacuolar H+-ATPase (V-ATPase) from bovine chromatin granules. The cleavage occurs in Golgi apparatus through furin or ADMA19. A sPRR ELISA kit has been developed to detect sPRR in plasma and urine samples. With this assay, increased serum sPRR levels have been demonstrated in patients with heart failure, kidney disease, hypertension, and preeclampsia. Moreover, serum sPRR is positively associated with serum creatinine, blood urea nitrogen, and urine protein and is inversely associated with the estimated glomerular filtration rate in patients with chronic kidney disease caused by hypertension and type 2 diabetes. However, serum sPRR was not correlated with serum renin, prorenin, or aldosterone in healthy subjects or in patients with diabetes and hypertension.

Within the kidney. PRR is expressed abundantly in the distal nephron, particularly in intercalated cells of the collecting duct (CD). A functional role of PRR in regulating renal aquaporin 2 (AQP2) expression and urine-concentrating capability has been revealed by analysis of mice with conditional deletion of PRR in the nephron and the CD. However, whether the antidiuretic action of CD PRR is conferred by sPRR remains elusive.

Liver X receptors (LXRs) are activated by oxidized cholesterol derivatives and belong to a family of nuclear receptors that form heterodimers with the retinoid X receptor to regulate transcription of target genes governing cholesterol, fatty acid, and glucose metabolism. LXRs consist of two isoforms, LXRα, which is abundantly expressed in liver, small intestine, kidney, macrophages, and adipose tissue, and LXRβ, which is expressed more ubiquitously. LXRs have an established role in reverse cholesterol transport which leads to cholesterol efflux from peripheral tissues to the liver. Interestingly, emerging evidence indicates a potential role of LXRs in the regulation of the renin-angiotensin system (RAS) and renal transporters such as Na-Pi transporters, OAT1, and epithelial Na+ channel (ENaC). The present study defined a biological function and signaling of sPRR in the regulation of fluid homeostasis and tested PRR/sPRR further as a target of LXRs in the kidney.

1. Results i. Biological Function of sPRR

A biological function of sPRR was indicated through the immunostaining of rat kidneys using antibodies against different domains of PRR. The cellular localization of renal PRR in rats was examined using two different antibodies: the antibody raised against the C-terminal domain of PRR (termed "anti-PRR-C antibody": Abcam) and another antibody against the N-terminal domain in the sPRR sequence (termed "anti-PRR-N antibody"). After the cleavage, sPRR is recognized by anti-PPR-N but not by anti-PRR-C. Anti-PRR-C antibody labeled AQP2-CD cells, e.g., the intercalated cells (FIG. 1C). Unexpectedly, the labeling with anti-PRR-N was found predominantly on the apical membrane of CD principal cells (FIGS. 1 A and B), overlapping with AQP2 (FIGS. 1 D and E), confirming the localization in principal cells but not in intercalated cells. The images from colabeling with anti-PRR antibody and anti-AQP2 antibody were merged (FIG. 1 G-I). A competition assay was performed to validate the specificity of anti-PRR-N antibody. The signal from this antibody disappeared after preincubation with a recombinant sPRR protein, sPRR-His (FIGS. 1 J and K) or with the immunizing peptide (FIG. 1L) or with the omission of primary antibody (FIG. 1M).

Figures 2A, 2B, 2C, 2D, 2E:
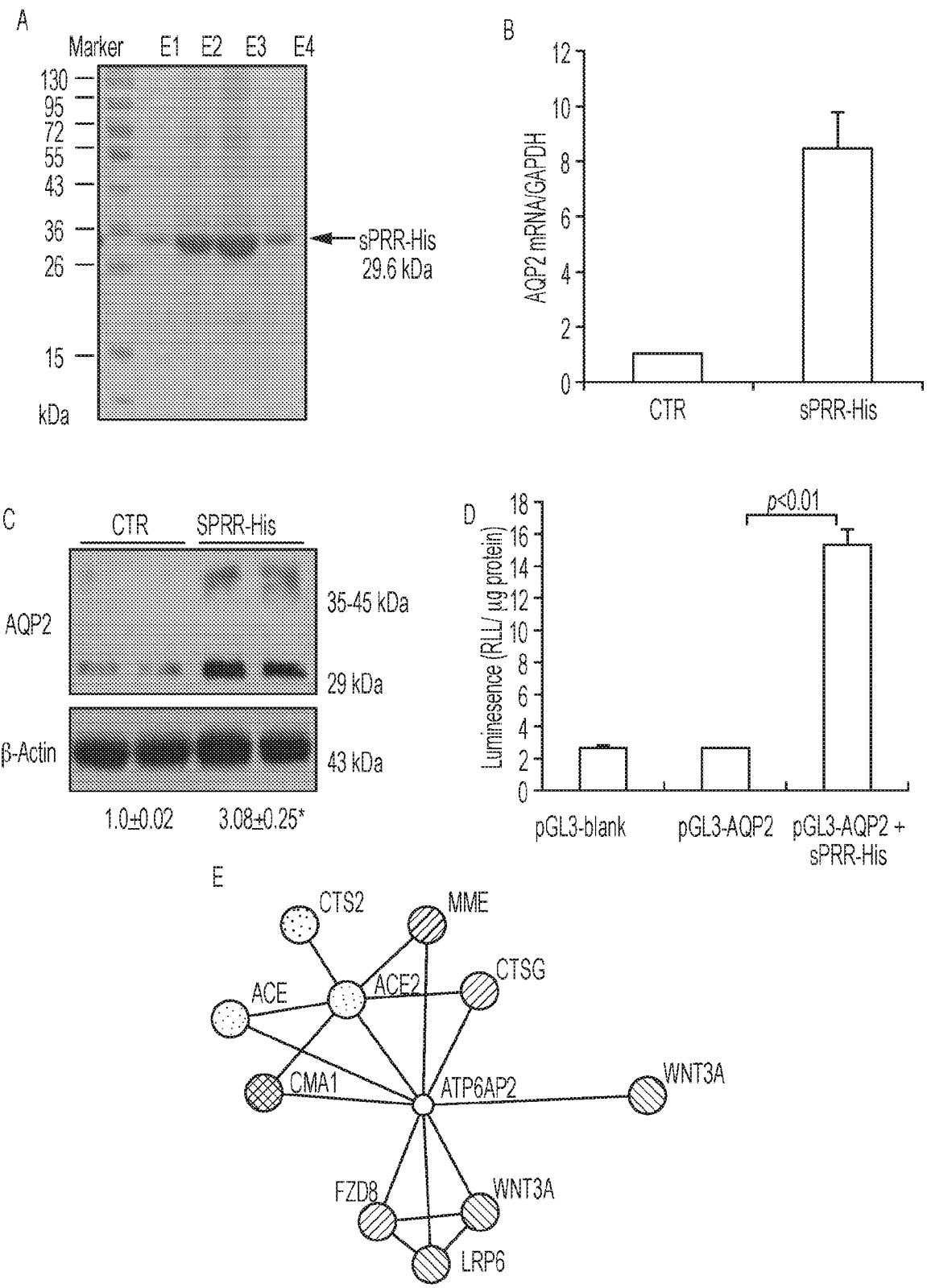
FIGS. 2A-2E shows the characterization of sPRR function. A recombinant PRR, sPRR-His, was expressed in a mammalian cell-expressing system as a fusion protein that contained sPRR, a histidine tag in the C terminus, and a secretion signal peptide in the N terminus. (A) sPRR-His was purified from the medium as a single 29.6-kDa band in 12% SDS/PAGE gel. E1-4 are sequential fractions from the elution. (B and C) Primary rat IMCD cells grown in Transwells were exposed to 10 nM sPRR-His for 24 h, and AQP2 expression was analyzed by quantitative RT-PCR and immunoblotting (n=5 per group). (D) In a separate experiment, the cultured CD cells were transfected with an AQP2-luciferase construct, were allowed to grow to confluence, and then were treated with vehicle or 10 nM sPRR-His for 24 h, and luciferase activity was assayed (n=5 per group). (E) STRING is a template-based algorithm for predicting protein-protein structure. STRING was used to identify proteins that interact with sPRR. This analysis revealed 10 hits: CTSG (cathepsin G), ACE2 (angiotensin 1-converting enzyme 2). CMA1 (chymase 1), MME (membrane metalloendopeptidase), ACE (angiotensin 1 converting enzyme 1), CTSZ (cathepsin Z), ENPEP (glutamyl aminopeptidase), FZD8 (frizzled family receptor 8), WNT3A (wingless-type MMTV integration 3A), and LRP6 (low density lipoprotein receptor-related protein 6). CTR, control.

These immunostaining results raised the notion that sPRR derived from intercalated cells or other tubules can act on an as yet unknown membrane receptor in principal cells to regulate tubular transport function. To test this possibility, a recombinant rat sPRR was generated using a mammalian cell expressing system. This protein contained sPRR with a secretion signal in the N terminus and an eight-histidine tag in the C terminus (termed "sPRR-His") and appeared as a single 29.6-kDa band on 12% SDS/PAGE gel (FIG. 2A). Primary cultures of rat inner medullary collecting duct (IMCD) cells in Transwells exposed to 10 nM sPRR-His for 24 h exhibited a remarkable increase in AQP2 expression at both mRNA and protein levels (FIGS. 2 B and C). In a separate experiment, murine immortalized cortical collecting duct (mpkCCD) cells were transiently transfected by a luciferase reporter construct, pGL3-AQP2. The transfected cells were treated for 24 h with 10 nM sPRR-His or vehicle. The sPRR-His treatment induced a 5.5-fold increase in luciferase activity (FIG. 2D). The in vitro findings confirmed a direct stimulatory effect of sPRR-His on AQP2 expression.

ii. sPRR Activation of the Wnt-β-Catenin Pathway in the CD.

Figures 3A, 3B, 3C, 3D:
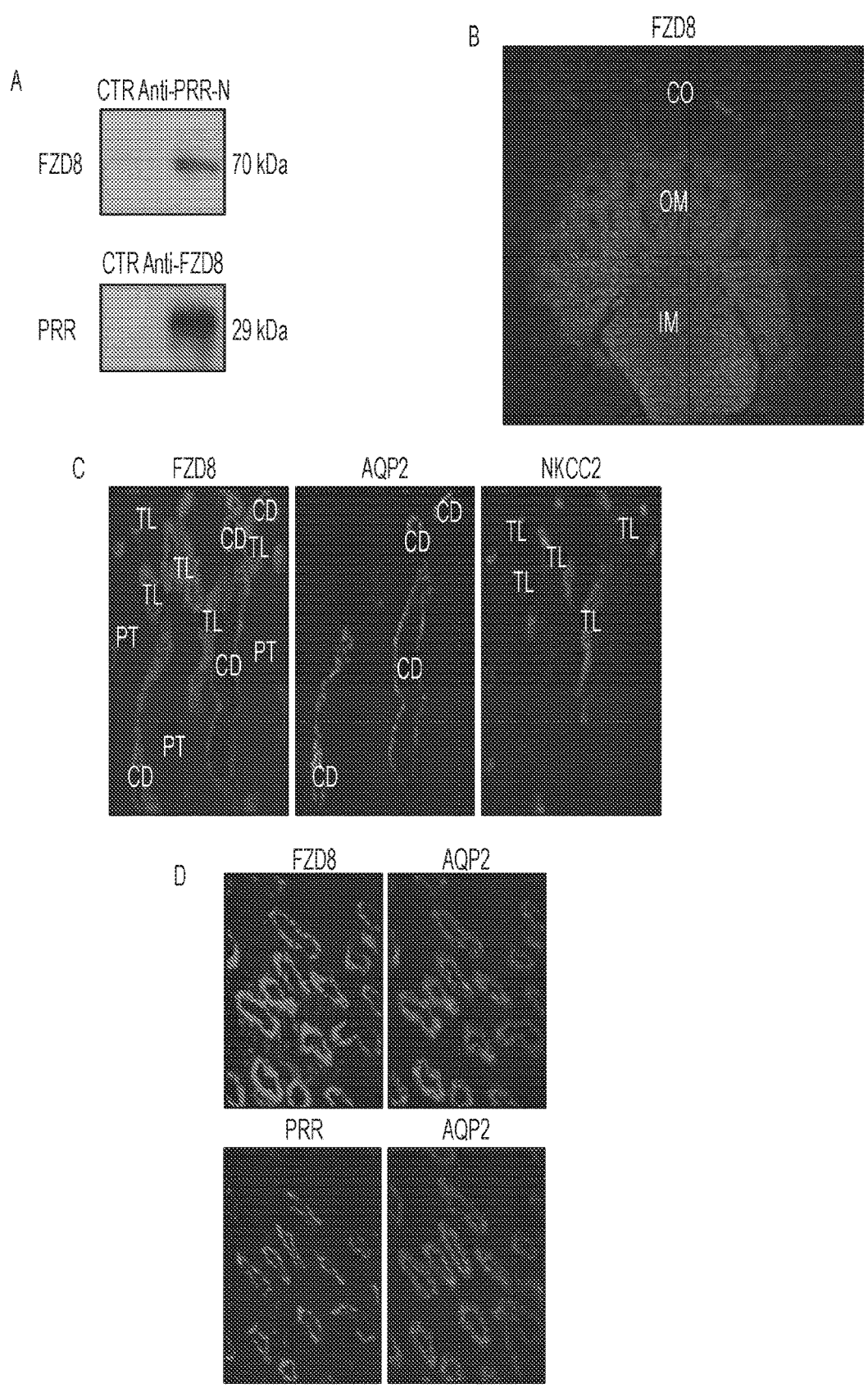

Search tool for the retrieval of interacting gene and proteins (STRING) is a template-based algorithm for protein-protein structure prediction. STRING was used to identify proteins that interact with sPRR. Among 10 candidate proteins, three are related to Wnt-β-catenin pathway: frizzled-8 (FZD8), low-density lipoprotein receptor-related protein 6 (LRP6), and Wnt-3a (FIG. 2E). Because FZD8 is a receptor component in the Wnt-O-catenin pathway, subsequent studies were focused on interaction between FZD8 and sPRR. Coimmunoprecipitation experiments using membrane fraction proteins prepared from the rat inner medulla demonstrated that sPRR binds to FZD8 (FIG. 3A). Immunostaining showed that at low magnification (FIG. 3B), FZD8 labeling was found predominantly in the outer and inner medulla with sporadic labeling in the cortex. Colabeling with AQP2 (the marker of CD principal cells) and labeling of consecutive sections for the electroneutral sodium, potassium and chloride cotransporters (NKCC2), a marker of thick ascending limb cells (FIG. 3C) confirmed FZD8 staining in the thick ascending limb and the CD. In the CD, FZD8 staining was detected in both principal and intercalated cells. The comparison between FZD8 and PRR labeling was made in the inner medulla where the two signals were roughly colocalized to the CD. In principal cells, both FZD8 and PRR were detected on the apical membrane although FZD8 labeling was relatively diffuse (FIG. 3D).

Figures 4A, 4B, 4C, 4D, 4E:
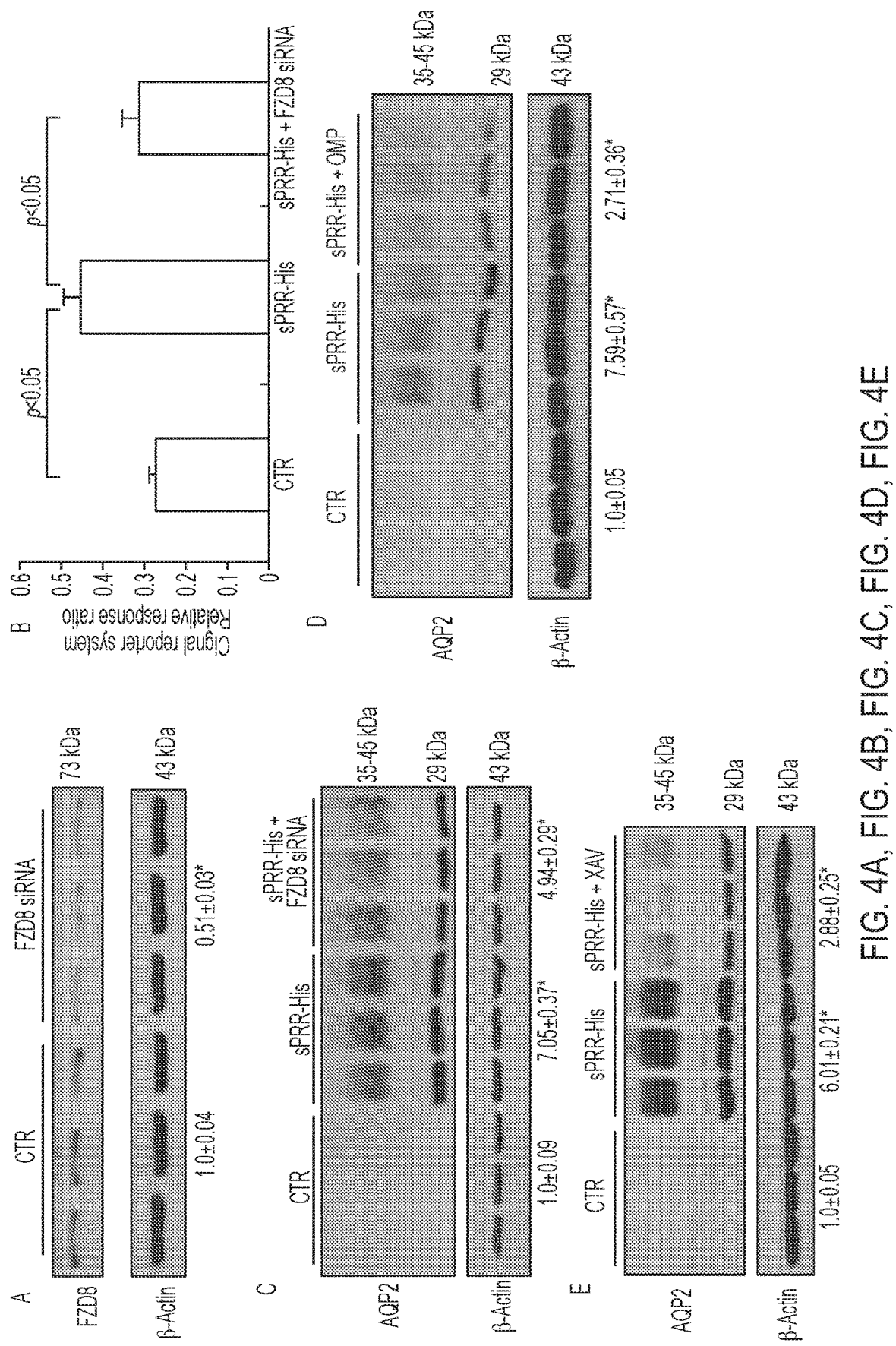
Figures 5A, 5B, 5C, 5D, 5E, 5F:
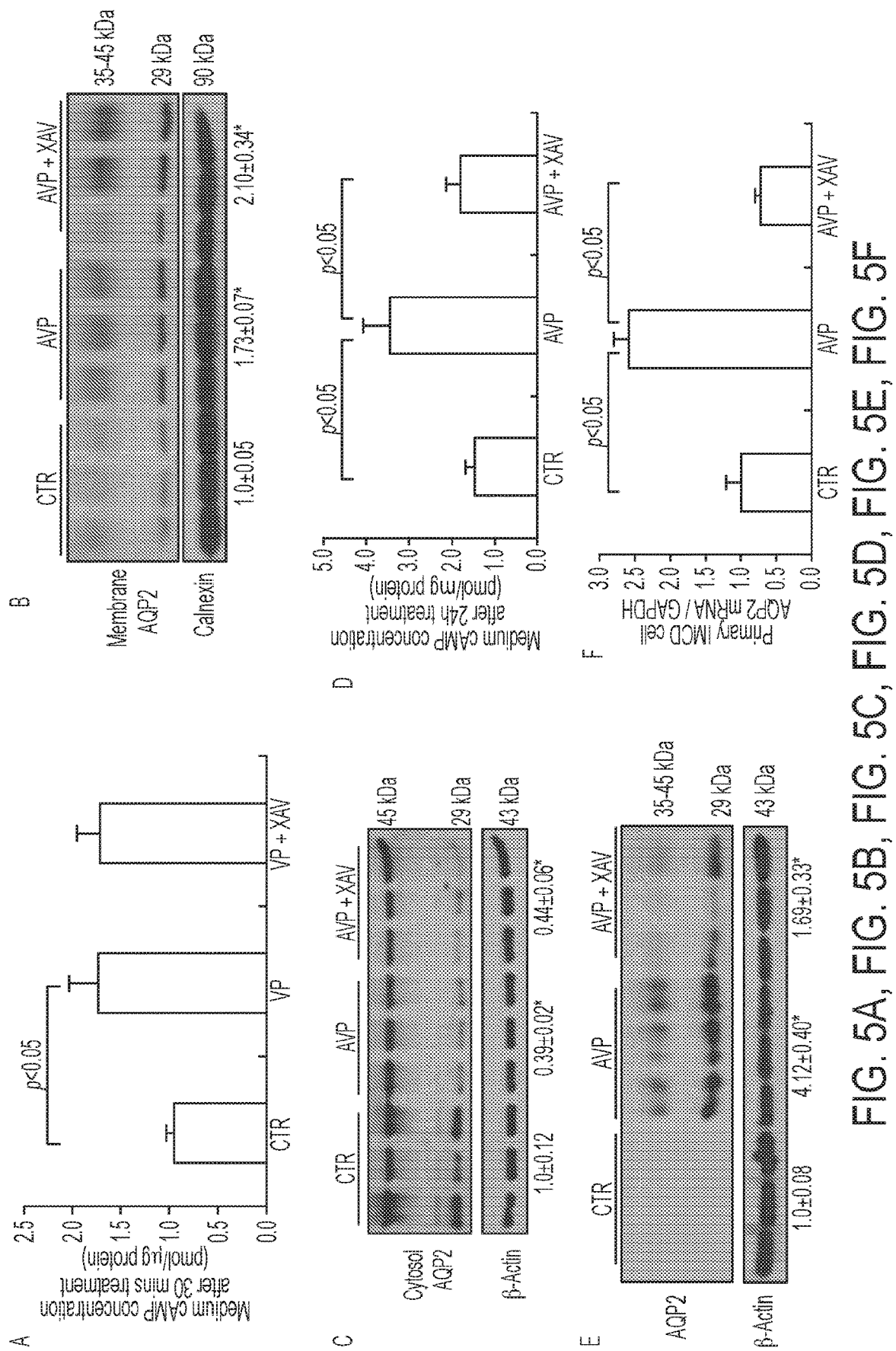
Figures 6A, 6B, 6C, 6D, 6E, 6F, 6G, 6H:
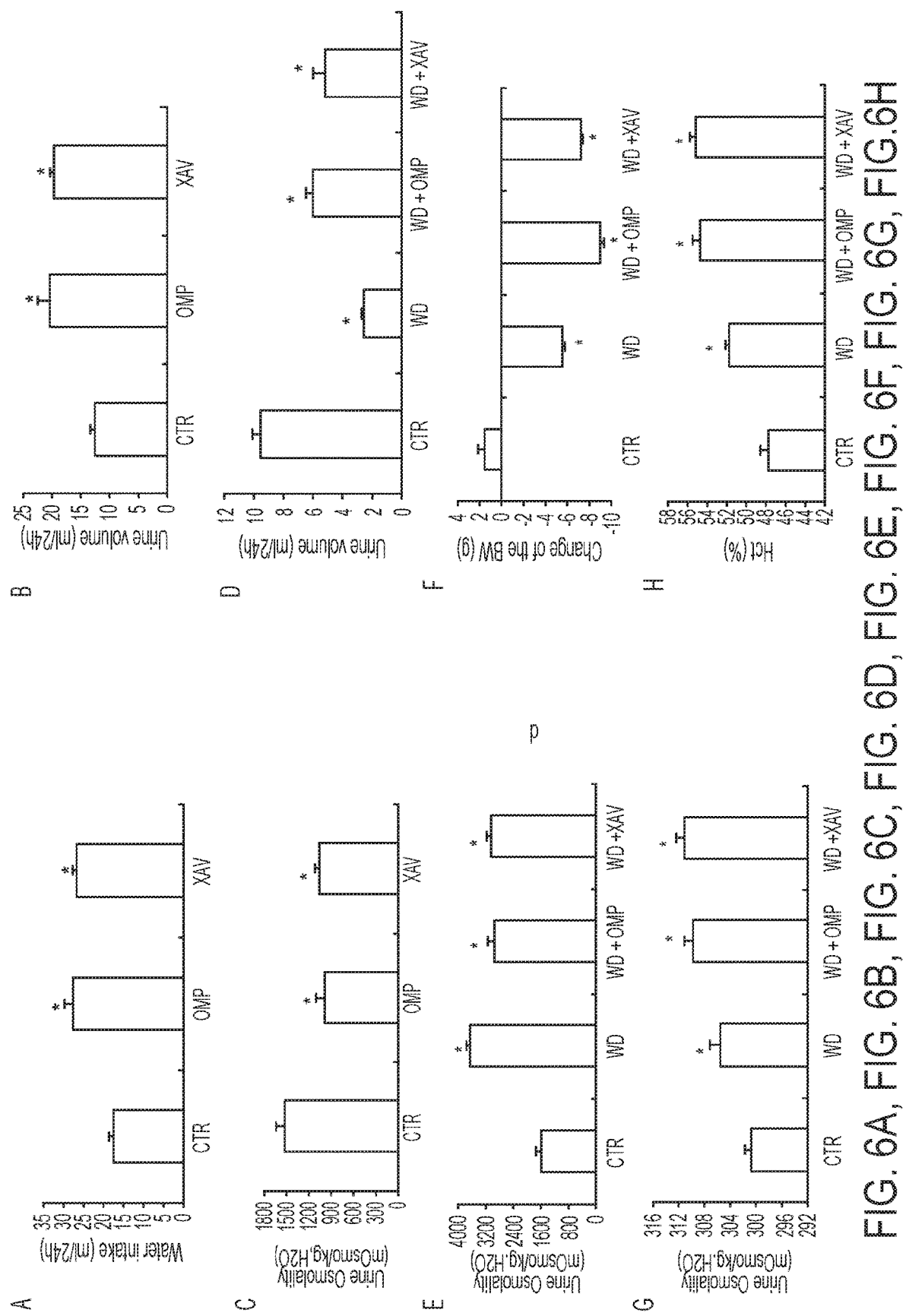
Figures 7A, 7B, 7C, 7D, 7E, 7F:
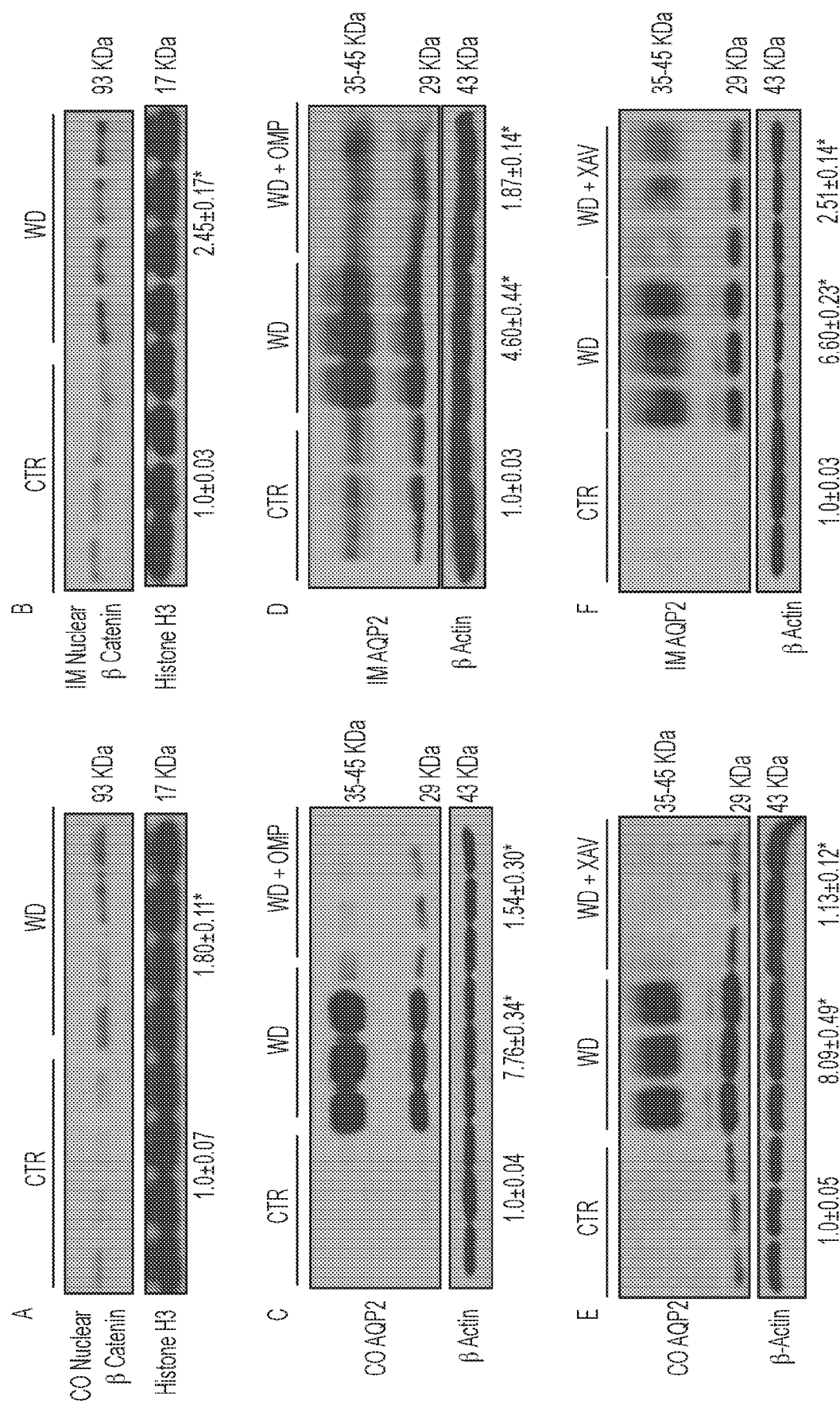

The functional role of FZD8 in mediating sPRR signaling in primary rat IMCD cells was assessed by using FZD8 siRNA and an FZD8 inhibitor, OMP-54F03 (OMP). The efficacy of FZD8 siRNA was validated by immunoblotting analysis of FZD8 protein expression (FIG. 4A). Exposure of rat IMCD cells to 10 nM sPRR-His for 24 h induced the activity of Wnt-responsive luciferase activity as assessed by using the Cignal TCF/LEF Reporter Assay kit (Qiagen), which was blunted by FZD siRNA (FIG. 4B). Consistent with this result, the sPRR-His treatment remarkably induced AQP2 protein expression, which was blunted by both FZD8 siRNA (FIG. 4C) and OMP (FIG. 4D) as well as by a tankyrase inhibitor XAV939 (XAV) (FIG. 4E) (26). Tankyrase belongs to the poly (ADP-ribose) polymerase family responsible for the transfer of ADP ribose from NAD+ to acceptor proteins and also for the activation of the Wnt-D-catenin pathway through the stabilization of the axin-β-catenin complex. The results indicate that sPRR signals through FZD8 to activate the Wnt/β-catenin pathway, leading to increased AQP2 expression.

Arginine vasopressin (AVP) is known to induce AQP2 trafficking to the apical membrane acutely (within minutes) by increasing phosphorylation of AQP2 and chronically (within hours) by stimulating AQP2 transcription, both through the cAMP-PKA pathway. It was found that the rapid rise of cAMP and the redistribution of AQP2 from the cytosol to the membrane in response to a 30-min exposure to AVP was unaffected by XAV treatment (FIG. 5 A-C); the trafficking event was evaluated by examining the abundance of AQP2 protein in the fractionated cell samples. Immunoblotting detected AQP2 protein as multiple bands of 35-45 kDa and 29 kDa, reflecting the glycosylated and nonglycosylated forms, respectively. In contrast, the increases in the cAMP level (FIG. 5D) and total protein abundance (FIG. 5E) and mRNA expression (FIG. 5F) of AQP2 were all effectively attenuated by XAV treatment. These results indicate that the Wnt-β-catenin pathway can specifically target AQP2 gene transcription but not AQP2 trafficking via selective coupling with the late but not early cAMP production after AVP treatment.

iii. The in Vivo Role of β-Catenin Signaling in Rats During Antidiuresis.

To probe the in vivo role of R-catenin signaling in fluid homeostasis, OMP and XAV were administered to Sprague-Dawley (SD) rats under basal conditions and during 48-h water deprivation (WD) and evaluated their impact on water balance. Under basal conditions, the administration of OMP and XAV over 48 h similarly induced polyuria, polydipsia, and hypoosmotic urine (FIG. 6 A-C). During 48-h WD, these treatments consistently increased urine volume and decreased urine osmolality, and these effects were accompanied by exaggerated weight loss (FIG. 6 D-F) and greater increases in plasma osmolality and hematocrit (Hct) (FIGS. 6 G and H). Immunoblotting showed that the abundance of β-catenin protein was increased in the nuclear fraction from both cortex and inner medulla following WD, indicating the activation of β-catenin signaling (FIGS. 7 A and B). AQP2 protein abundance in both renal cortex and inner medulla was increased remarkably following WD; this increase was attenuated significantly by both OMP and XAV (FIG. 7 C-F).

iv. Therapeutic Potential of sPRR-his for Treatment of Nephrogenic Diabetes Insipidus, Nephrogenic Diabetes Insipidus (NDI) is commonly caused by mutations of the vasopressin 2 receptor (V2R) gene: a specific therapy for this disease is lacking. The therapeutic potential of sPRR-His was explored in a mouse model of NDI induced with a V2R antagonist. OPC. sPRR-His was chronically infused via a catheter placed in the jugular vein driven by an osmotic minipump. After 7 d of sPRR-His infusion, OPC was given via gavage at 30 mg kg-' ' for 3 d. Administration of the V2R antagonist resulted in symptoms of ND including polydipsia, polyuria, and hypoosmotic urine, all of which were attenuated by sPRR-His treatment (FIG. 8 A-C). This result supports the therapeutic potential of sPRR for management of the symptoms of NDI. In the OPC-treated mice, urinary sPRR excretion was suppressed significantly (FIG. 8D), providing a rationale for the use of exogenous sPRR to treat NDI. This result also indicates that the production of renal sPRR can be under the direct control of the AVP-V2R pathway. In support of this notion, it has been shown that exposure of the CD cells to AVP stimulates the release of sPRR. FIG. 8E provides a schematic illustration of the mechanism of action of sPRR in the CD principal cells. The data indicates that sPRR binds FDZ8, leading to the activation of β-catenin that promotes chronic cAMP accumulation, ultimately enhancing AQP2 transcription.

v. Induction of Diabetes insipidus and Suppression of Renal PRR by LXR Agonism.

Besides their well-recognized role in regulating lipid and glucose metabolism, LXRs are potential regulators of the RAS and fluid balance. The hypothesis that LXRs may affect renal PRR expression and local RAS and hence fluid homeostasis was tested. In the initial experiment, the effects of the LXR agonist TO901317 on fluid homeostasis and on renal PRR and urinary renin levels were examined in mice. A 7-d treatment with TO901317 in C57BL6 mice reduced body weight (32.36±0.63 vs. 28.61±0.36 g, P<0.05) and food intake (4.08±0.19 vs. 3.54±0.15 g, P<0.05), although to a lesser extent. This treatment led to severe polyuria (FIG. 9A) and hypoosmotic urine (FIG. 9B), indicating a urine concentrating defect. The expression of renal PRR protein and the excretion of urinary sPRR were examined by immunoblotting and ELISA, respectively. Both renal PRR expression (FIGS. 9 C and D) and urinary sPRR excretion (FIG. 9E) were suppressed consistently by TO901317. This experiment indicated that the suppressed renal PRR level can be responsible for T901317-induced diabetes insipidus (DI).

Figures 9A, 9B, 9C, 9D, 9E, 9F, 9G, 9H, 9I:
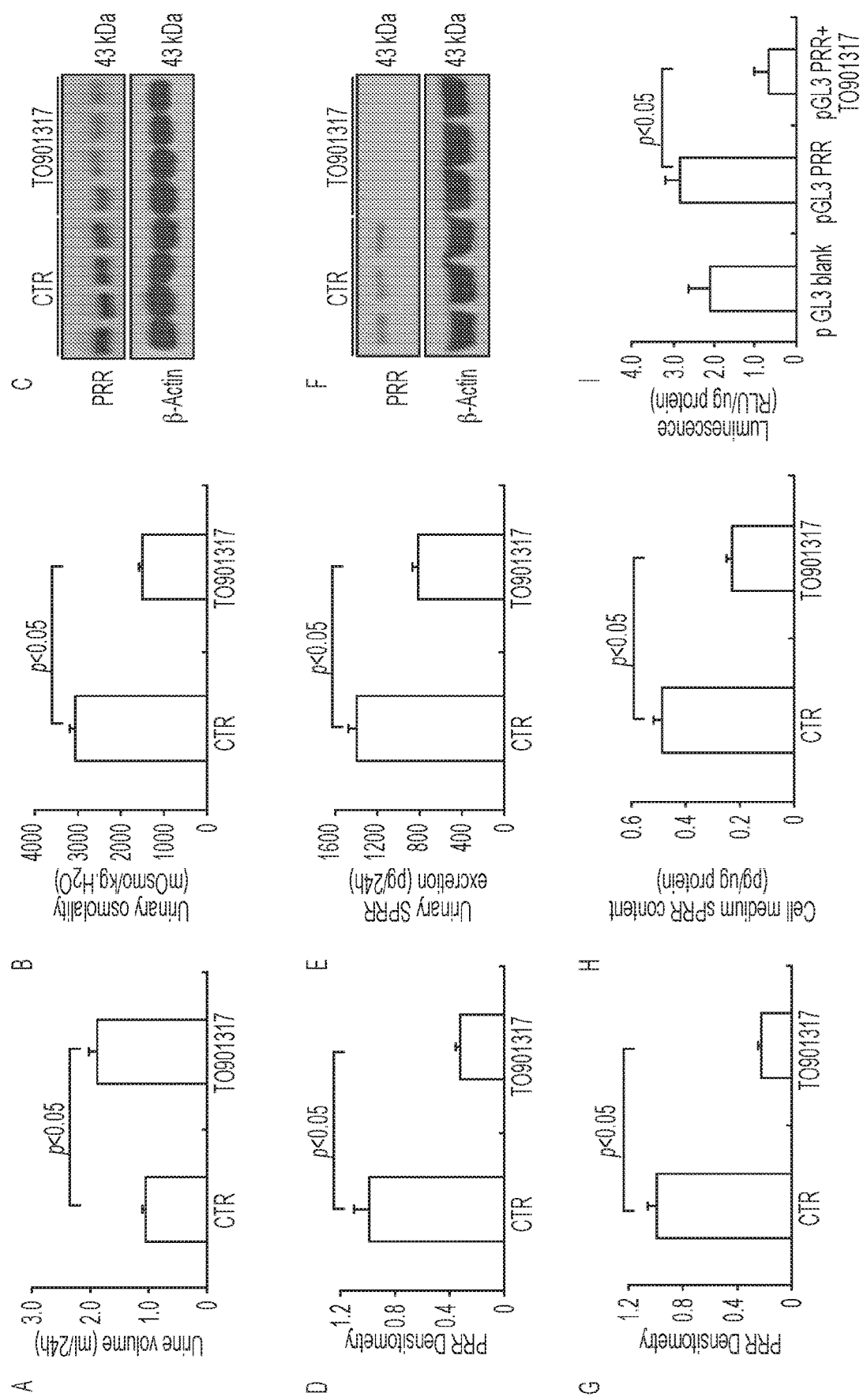
Figures 10A, 10B, 10C, 10D, 10E:
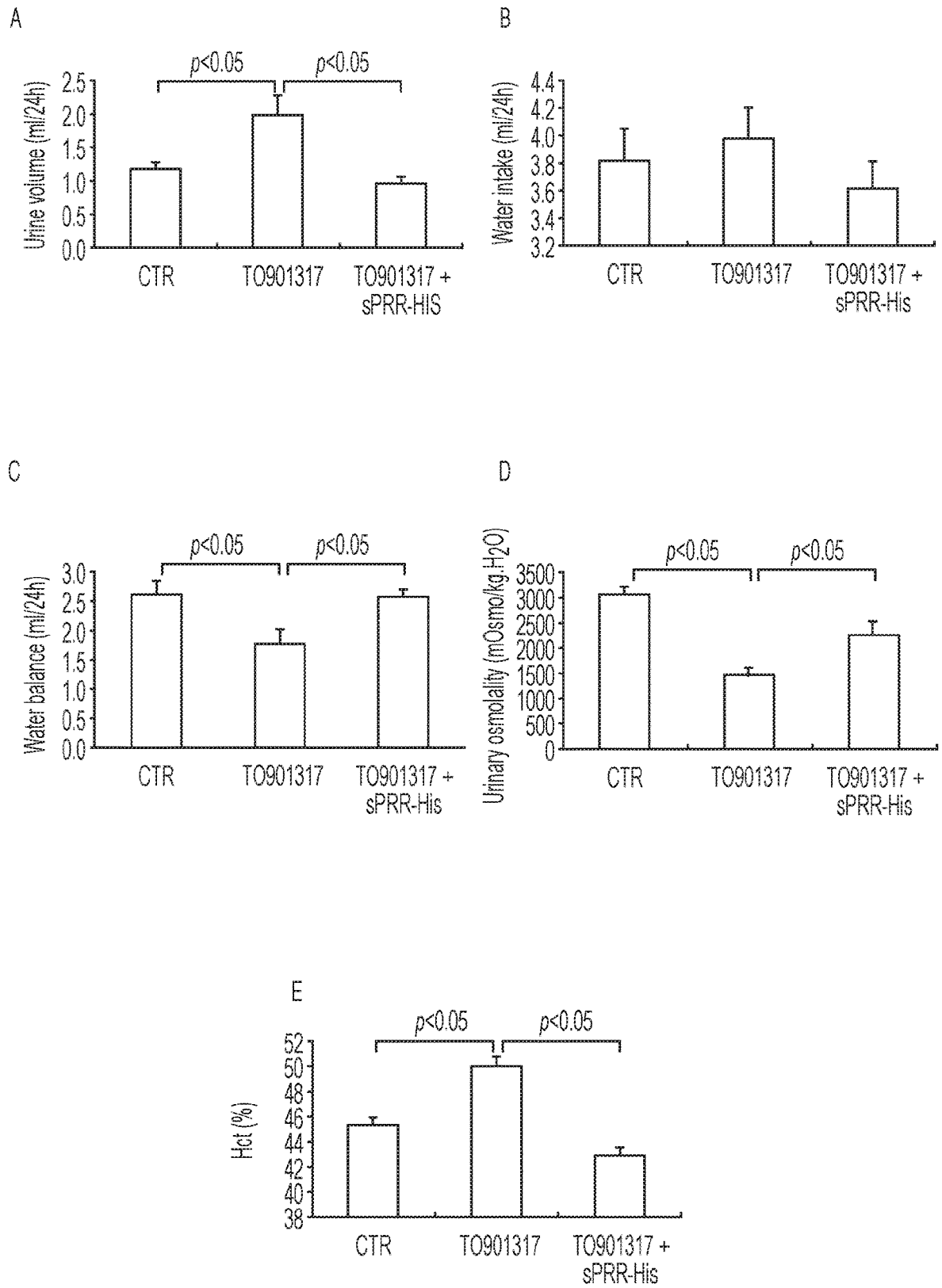

Cell-culture experiments were performed to examine the direct effect of TO901317 on PRR expression. mpkCCD cells were exposed to TO901317 or vehicle for 24 h, and PRR protein expression was determined by immunoblotting. TO901317 treatment reduced PRR protein expression by 85% (FIGS. 9 F and G) and medium sPRR by 60% (FIG. 9H). In a separate experiment, mpkCCD cells were transiently transfected by a pGL3-PRR construct. The transfected cells were treated with TO901317 or vehicle for 24 h. TO901317 treatment suppressed luciferase activity by 76% (FIG. 9I). The in vitro findings confirmed that TO901317 has a direct inhibitory effect on PRR expression.

vi. sPRR-His Attenuates TO901317-induced DI in Mice.

Figures 11A, 11B, 11C, 11D, 11E:
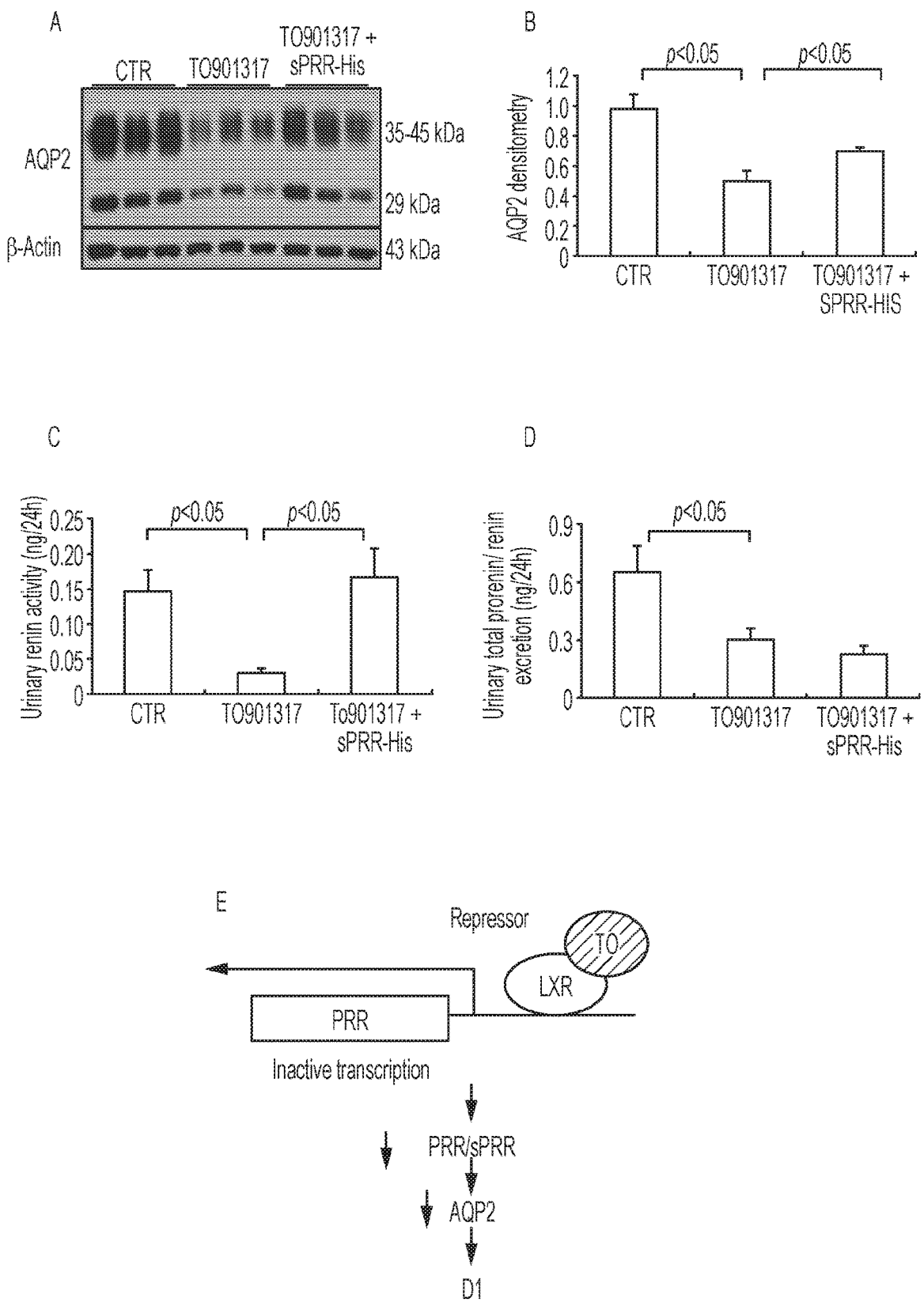

In the subsequent experiment, a more detailed analysis of TO901317-induced DI was performed and the causal role of suppressed renal PRR was further examined in this phenomenon. This experiment comprised three groups: control, TO901317-treated, and TO901317+sPRRHis-treated mice. TO901317-treated mice displayed polyuria, polydipsia, decreased water balance, hypoosmotic urine, and plasma volume contraction (as reflected by the rise in Hct), confirming the urine-concentrating defect (FIG. 10). All these parameters were improved significantly in mice treated with TO901317+sPRR-His (FIG. 10). Of note, water balance was determined by subtracting urine volume from water intake. AQP2, a major water channel on the apical membrane of the CD, plays a key role in determining urine-concentrating capability. Immunoblotting demonstrated that TO901317 significantly reduced renal AQP2 expression, which was partially restored by sPRR-His (FIGS. 11 A and B). sPRR-His can affect the intrarenal RAS, and this effect can be reflected by urinary renin activity. Urinary renin activity, as assessed by measuring the generation of angiotensin I (AngI), was suppressed by TO901317, and the suppression was completely reversed by sPRR-His (FIG. 1C). ELISA was also performed to determine the prorenin/renin concentration in the urine. Although urinary prorenin/renin excretion was suppressed by TO901317, it was unaffected by sPRRHis (FIG. 11D). This result is compatible with the concept that sPRR regulates renin primarily at its activity level (3). FIG. 11E provides a schematic illustration of the mechanism by which TO901317 induces DI. Upon binding to TO901317, LXRs function as a transcriptional repressor to inactivate PRR transcription. The reduced PRR/sPRR levels down-regulate AQP2 expression, Leading to DI.

2. Discussion sPRR is generated by protease-mediated cleavage in the Golgi apparatus and is released to plasma or urine. Serum sPRR levels are elevated in various pathological states. Pharmacological and conditional gene-knockout approaches were used to demonstrate that CD PRR has an essential role in determining renal AQP2 expression and urine-concentrating capability. In the present study, it was discovered that sPRR acts via FZD8-dependent activation of β-catenin signaling that leads to increased AQP2 expression and thus enhanced urine concentrating capability. In addition, LXR agonism with TO901317 induced DI by inhibiting the renal PRR and the intrarenal RAS.

A stimulatory effect of sPRR-His on AQP2 expression in cultured rat IMCD cells grown in Transwells was found. In this experiment, sPRR-His was used at 10 nM, which is likely a physiological concentration. Moreover, the signaling mechanism of sPRR-His up-regulation of AQP2 was examined, revealing the involvement of FZD8-dependent β-catenin signaling. This indicated an interaction between sPRR and FZD8 was obtained by a template-based algorithm for predicting protein-protein structure. The physical interaction of the two proteins in the membrane fraction of the rat inner medulla was confirmed by coimmunoprecipitation. The interaction also was demonstrated at a functional level, because inhibition of FZD8 by siRNA and pharmacological approaches effectively attenuated the stimulatory effect of sPRR-His on AQP2 in cultured CD cells. The functional role of FZD8 in regulating renal AQP2 expression and urine-concentrating capability was confirmed in vivo by using a FZD8 inhibitor, OMP. The antidiuretic function of FZD8 was supported by the similar effect of a general Wnt/0-catenin inhibitor, XAV. Immunostaining demonstrated that FZD8 is localized to the CD and thick ascending limb, as is consistent with the nephron-distribution pattern of PRR. Within the CD, FZD8 labeling was found in both principal and intercalated cells, a pattern not exactly same as sPRR labeling. FZD8 can serve a function beyond its association with sPRR. These results agree with a previous report that β-catenin signaling mediated AVP-induced AQP2 expression in mpkCCDc14 cells. It is evident that β-catenin signaling is actively involved in the physiological regulation of fluid homeostasis through coupling with sPRR.

A large body of evidence has demonstrated that PRR serves as a component of the Wnt receptor complex to regulate embryogenesis in low vertebrates in which the RAS does not exist. It is evident that PRR acts in a renin-independent manner in low vertebrates. PRR appears to be similarly involved in the regulation of embryogenesis in mammals, as evidenced by the lethal phenotype in mice with systemic or tissue-specific deletion of PRR. A large number of studies have challenged the physiological function of PRR and its relationship with the RAS). Whether an intrinsic linkage between the RAS and the developmental β-catenin pathway occurs in mammals in settings of development or physiology is unknown. These results link prorenin/sPRR to the β-catenin pathway in the kidney during physiological regulation of fluid homeostasis.

The cAMP-PKA pathway is the principle mediator of AVP induced AQP2 trafficking and transcription. An issue arises as to whether the Wnt-4-catenin pathway interacts with the cAMP-PKA pathway during AVP-induced signaling. Inhibition of the Wnt-4-catenin pathway did not affect AQP2 trafficking to the membrane fraction or cAMP production induced by 30-min exposure to AVP. In contrast, this maneuver did block AQP2 expression and cAMP production induced by 24-h AVP treatment. These results indicate that activation of the Wnt-β-catenin pathway can be involved primarily in sustaining the cAMP production during prolonged AVP treatment to increase AQP2 transcription. This mechanism does not appear to be required for the regulation of AQP2 trafficking, which is a rapid response to AVP. There is a wealth of information regarding the role of the cAMP-PKA pathway in this acute response to AVP, but relatively little is known about this pathway in a chronic setting of AVP treatment. The present study delineates a unique role for β-catenin signaling in chronic but not acute regulation of the cAMP-PKA-AQP2 axis.

Multiple previous studies, as well as this one, consistently demonstrate that, within the CD, PRR is detected in intercalated cells by using antibody against the C terminus of PRR (anti-PRR-C antibody). A question arises as to how intercalated cell-derived PRR up-regulates AQP2 expression in the principal cells. This regulation can be through a paracrine mechanism, and there is an intriguing possibility that sPRR can serve as a mediator of the communication between the two cell types in the CD. An antibody against the epitope in the sPRR, anti-PRR-N antibody, stained only principal cells but not intercalated cells or other non-CD tubules that are known to express PRR. More direct evidence came from cell-culture experiments showing that exposure of rat IMCD cells to sPRR-His in the nanomolar range induced a remarkable increase in AQP2 expression mimicking the effect of prorenin. This result indicates that sPRR has a physiological function.

The current therapy for DI is suboptimal. Although supplementation of AVP is effective for central DI, no specific therapy is currently available for nephrogenic DI. The present study demonstrates the therapeutic potential of sPRR-His in a mouse model of nephrogenic DI induced by V2R antagonism. Because sPRR acts downstream of V2R, it also should be effective for treatment of central DI.

A large body of evidence has established a link between energy metabolism and fluid balance. A high-energy state, such as obesity, is associated with disturbance of electrolytes and fluid balance and hypertension, whereas a low-energy state, such as fasting, induces natriuresis and diuresis. Along this line, activation of PPARγ, a key regulator of glucose metabolism and adipogenesis, causes body weight gain and plasma volume expansion. In the present study, it was determined that LXR against TO901317 exerted a profound diuretic action in mice as indicated by polyuria, polydipsia, hypoosmotic urine, and contraction of plasma volume. AQP2, a major water channel on the apical membrane of the CD, was remarkably suppressed, likely conferring the diuretic action of TO901317.

In light of sPRR's action as a key regulator of AQP2 expression and urine-concentrating capability, PRR/sPRR was suspected to be a molecular target of LXRs in the kidney. In vivo data showed a significant reduction of renal PRR expression and urinary sPRR excretion in TO901317-treated mice, and the administration of sPRR-His completely rescued TO901317-induced DI. Consistent with this observation, in vitro data demonstrated that TO901317 had a direct inhibitory effect on PRR expression and PPR-luciferase activity in cultured CD cells. These results demonstrate that LXRs can function as a transcriptional repressor of the PRR gene. It is interesting that LXRβ−/− mice display central DI caused by the impairment of AVP production (33). This phenotype indicates an antidiuretic action of LXRβ, which is the opposite of the diuretic action of TO901317. Diuretic action of TO901317 can be conferred mainly by LXRα. This possibility needs to be validated in future studies using LXRα-null mice.

It has been shown that acute LXR activation induces a transient increase in renin transcription in the juxtaglomerular cells, but its chronic activation remarkably suppresses the expression of renin, AT1R, and angiotensin 1-converting enzyme 1 (ACE) in the heart and kidney following isoproterenol treatment. In agreement with the inhibitory effect of LXRs on local RAS, TO901317 treatment was found to suppress urinary renin, an index of the intrarenal RAS). Although LXRs can function as a negative regulator of renin expression at the juxtaglomerular apparatus in the acute setting, they appear primarily to suppress PRR and the local RAS to elicit a diuretic response.

In summary, the present study reports a biological function of sPRR in regulating fluid homeostasis. sPRR is associated with FZD8 to activate β-catenin, which interacts with the cAMP-PKA pathway to induce AQP2 expression and enhance the urine-concentrating capability. Because intercalated cells are the potential source of sPRR, and principal cells are the site of its action, it seems reasonable that sPRR mediates the communication between the two cell types in the CD. Last, the diuretic action of the LXR agonist T901317, which is conferred by inhibition of the renal PRR/sPRR system.

3. Methods i. Animals

Male 10- to 12-wk-old SD rats and C57BL6 mice were purchased from Charles River Laboratories and the Jackson Laboratory, respectively. All animals an estimated level of 50 mg-kg body weight–1·d–1. All mice were placed in metabolic cages, and 24-h water intake and urine output were recorded and collected at the end of the experiments.

ii. Cell-Culture Experiments

For sPRR signaling studies, primary IMCD cells were prepared from 4-wk-old SD rats as previously described (35). The cells were grown in Transwell plates (catalog no. 29442-074; VWR International) with DMEM/F-12 medium containing 10% (vol/vol) FBS, 0.5 μM 8-Br-cAMP, 130 mMNaCl, and 80 mMurea. Upon confluence, the cells were serum deprived for 12 h and pretreated with an inhibitor (10 μM XAV or 10 μM OMP) followed by 24-h treatment with AVP (10 nM) or sPRR-His (10 nM). At the end of the experiments, the medium was collected for biochemical assays.

The effect of TO901337 on PRR expression was tested in mpkCCD cells. These cells were grown to confluence in six-well plates. After 12-h serum deprivation, the cells were treated with vehicle or 10 μM TO901317 for 24 h and then were harvested for analysis of PRR expression and sPRR release. In a separate experiment, mpkCCD cells at ~50% density were transiently transfected with a construct containing the luciferase gene under the control of the 2,016-bp 5' flanking region of the PRR gene. Upon confluence, the transfected cells were treated for 24 h with vehicle or 10 μM T901317 and then were harvested for analysis of luciferase activity.

iii. Enzyme Immunoassay.

Urinary or medium sPRR was determined using a commercially sPRR enzyme immunoassay (EIA) kit (catalog no. JP27782; Immuno-Biological Laboratories) according to the manufacturer's instructions.

iv. Immunofluorescence Staining.

The tissues were fixed in 10% neutral buffered formalin for 24 h and then were embedded in paraffin. After deparaffinization, thin sections (4 μm) were processed for double-labeling with immunofluorescence. For antigen recovery, the slides were immersed in Tris HC EDTA buffer (pH 9.0) at a high temperature (98° C.) for 12 min. The slides were blocked in 1% (wt/vol) BSA for 1 h and then were incubated overnight with primary antibody at 4° C. After the primary antibody was washed off, sections were incubated for 1 h at room temperature with donkey anti-goat-IgG-FITC (Santa Cruz) or donkey anti-rabbit IgG-TRITC (Life Technologies). Rabbit anti-PRR antibody from Abcam was raised against residues 335-350 in the C terminus (termed "anti-PRR-C antibody"). A second anti-PRR antibody used in the present study raised against residues 218-235 in the N terminus of PRR (termed "anti-PRR-N antibody") was generated in Y.F.'s laboratory (24). Goat anti-AQP2 antibody was purchased from Santa Cruz. Rabbit anti-NKCC2 antibody was purchased from Stress-Marq Biosciences Inc.

v. Immunoblotting.

Renal tissues were lysed and subsequently sonicated. Protein concentrations were determined using Coomassie reagent. Forty micrograms of protein from each sample were denatured in boiling water, separated by SDS/PAGE, and transferred onto nitrocellulose membranes. Blots were blocked 1 h with 5% nonfat dry milk in Tris-buffered saline (TBS), followed by overnight incubation with primary antibody. After washing with TBS, blots were incubated with goat anti-rabbit/mouse HRP-conjugated secondary antibody and visualized using ECL. The blots were quantitated by using Image-Pro Plus (Media Cybernetics). The primary antibodies were goat anti-AQP2 antibody, rabbit anti-PRR-N antibody, and rabbit anti-FZD8 antibody (all from Santa Cruz), rabbit anti-V2R antibody (Abcam), and goat anti-β-catenin antibody (Novus).

vi. Quantitative RT-PCR.

Total RNA was isolated from renal tissues and reverse transcribed to cDNA. Oligonucleotides were designed using Primer3 software (bioinfo.ut.ee/primer3-0.4.0/). Primers of AQP2 were 5'-gctgtcaatgctctccacaa-3' (sense) and 5'-ggagcaaccggtgaaataga-3' (antisense); primers for GAPDH were 5'-gtcttcactaccatggagaagg-3' (sense) and 5'-tcatggatgaccttggccag-3' (antisense).

vii. Cell Membrane and Cytoplasmic Protein Fraction Isolation.

The membrane and cytosolic fractions of proteins were extracted using a kit according to the manufacturer's instructions (catalog no. BSP002; Bio Basic Inc.).

viii. Coimmunoprecipitation.

For coimmunoprecipitation with PRR and FZD8, the membrane fraction of rat renal inner medullary was performed using a kit (catalog no. BSP002; Bio Basic Inc.). Anti-PRR-N (from Y.F.) or anti-FZD8 (Santa Cruz) antibody was cross-linked with the magnetic beads (catalog no. 88805; Pierce) and then incubated for 30 min with the renal medullary membrane proteins. The beads were collected, washed, and eluted. The immunoprecipitated samples were analyzed for the binding partner by immunoblotting.

ix. siRNA or Plasmid Transfection in Primary Cultured IMCD Cells.

IMCD cells were transfected with FZD8 siRNA oligonucleotides (Invitrogen) or the luciferase reporter plasmid (catalog no. CCS-018L; Qiagen) at a final concentration of 5 nM using HiPerFect transfection reagent (catalog no. 301702; Qiagen) for 72 h. The efficiency of FZD8 knockdown was validated by immunoblotting of FZD8. For the luciferase assay, each sample consisted of a positive control, a negative control, and a target luciferase construct, and the reporter activity was calculated according to the manufacturer's instruction.

x. Preparation of Luciferase Constructs.

Genomic DNA was extracted from rat tail using a Tissue DNA kit (D3396-01; Promega). A 2,016-bp fragment of the 5' flanking region of the PRR gene (GenBank accession no. NM_001007091; 1,941±75 bp) was amplified from the rat genomic DNA by PCR and subcloned to the pGL3-Basic reporter vector (Promega) using NheI and BgIII restriction sites; this construct was termed "pGL3-PRR." A 2,084-bp fragment of the 5' flanking region of the AQP2 gene (GenBank accession no. NM_012909; 2,000±84 bp) was cloned to the pGL3-Basic reporter vector by a similar strategy; this construct was termed "pGL3-AQP2." The identity of these constructs was validated by sequencing.

xi. Luciferase Assay.

The mpkCCD cells were transfected with pGL3-AQP2 plasmid or empty vector by using HiPerFect Transfection Reagent (catalog no. 301702; Qiagen). Upon confluence, all cells were starved for 12 h; then pGL3-PRR- and pGL3AQP2-transfected cells were treated for 24 h with TO901317 (10 µM) or sPRR-His (10 nM), respectively. The vehicle-treated group served as a control. The luciferase activities were measured using a luciferase assay system (Promega), and luminescence was detected by using an illuminometer (BMG FLUOstar OPTIMA).

xii. Statistical Analysis.

Data are summarized as means±SE. Statistical analysis was performed using ANOVA with the Bonferroni test for multiple comparisons or paired or unpaired Student's t test for two comparisons. $P<0.05$ was considered statistically significant.

B. The Therapeutic Use of Soluble (Pro)Renin Receptor (Pro)renin receptor (PRR) is a new component of the renin-angiotensin system. A 28 kDa soluble form of PRR (sPRR) can be generated by intracellular cleavage by furin and secreted in plasma. A large number of clinical studies indicate importance of circulating sPRR. By ELISA, serum levels of sPRR are increased during pregnancy and in patients with heart failure, gestational diabetes mellitus, obstructive sleep apnea syndrome, primary epithelial ovarian cancer. In this study, a histidine-tagged recombinant sPRR was generated, termed as sPRR-His, and examined its effect on aquaporin-2 (AQP2) expression in primary IMCD cells and urine concentrating capability in vivo. sPRR-His at the nanomolar range induced AQP2 mRNA and protein expression and enhanced urine concentrating capabilities and therefore can treat nephrogenic diabetes insipidus.

1. Methods i. Animals

Two-month-old male C57/BL6 mice were purchased from Jason Laboratory. The animals were fed a normal or high fat diet for 8 months. The high fat-fed animals were divided to receive vehicle or sPRR-His infusion via a catheter placed in the jugular vein and the other end of the catheter connected to osmotic mini-pump.

ii. Insulin Tolerance Test (ITT) and Glucose Tolerance Test (GTT)

These tests are performed in order to evaluate insulin sensitivity and glucose metabolism. An insulin tolerance test is designed to determine the sensitivity of insulin-responsive tissues in the rodent. This is determined by measurement of glucose remaining in the circulation over time after a bolus intra-peritoneal (IP) insulin injection. After 6 h fasting, under isoflurane anesthesia, insulin (0.25 U/kg body weight) is administered, one drop of blood (~5 µl) was collected via a tail tip cut and transfer directly onto a glucose indicator strip at 0, 15, 30, 60 and 90 min. At the end of the experiment, wipe tail with 70% alcohol and allow drying. Ensure that blood loss from the tail stopped before placing the animal back to its cage. The glucose tolerance test measures the clearance of an IP injected glucose load from the body. It is used to detect disturbances in glucose metabolism that can be linked to diabetes or metabolic syndrome. After 6 h fasting, fasted blood glucose levels are determined before a solution of glucose is administered by IP injection. Subsequently. The blood glucose level is measured at different time points during the following 90 minutes as described above for ITT test. The proposed ITT and GTT tests can apply to all strains of animals in this protocol particularly if they develop signs of metabolic syndrome or abnormalities in plasma glucose or insulin.

iii. Insulin ELISA Assay

Insulin was measured with a commercial kit (Ultra-Sensitive Mouse Insulin ELISA Kit, Crystal Chem, #90080). Blood was collected and centrifuged. Plasma was used for the following test. Insulin in the sample is bound to the guinea pig anti-insulin antibody coated on the microplate wells. After washing, horse radish peroxidase (HRP)-conjugated anti-insulin antibody was then added. These enzyme-labeled antibodies form complexes with the previously bound insulin. The bound HRP conjugate in the microplate well is detected by the addition of the TMB substrate. Measure the absorbance at 450 nm.

iv. Albumin Assay

Mouse urinary albumin was measured with a commercial kit (Mouse Albumin ELISA Kit, GenWay, #GWB-282C17). The urinary albumin reacts with the anti-Albumin antibodies coated on the microplate wells. After washing, horse radish peroxidase (HRP)-conjugated anti-albumin antibody was then added. These enzyme-labeled antibodies form complexes with the previously bound albumin. The bound HRP conjugate in the microplate well is detected by the addition of the TMB substrate. Measure the absorbance at 450 nm.

2. Results

In the current study, the effect of sPRR-His, a recombinant soluble (pro)renin receptor, was tested on obesity and obesity-related conditions in high fat diet-fed male C57/BL6 mice. The mice were treated with high fat diet for 8 months (DIO). During the last two weeks, the DIO mice were randomly divided to receive vehicle or sPRR-His via intravenous infusion driven by osmotic mini-pump. The DIO model induced by a long-term high fat diet developed severe obesity associated with increased glucose and insulin resistance, abnormal lipid profile, and fatty liver. The 2-wk sPRR-His treatment significantly reduced body weight (FIG. 12). The perirenal fat mass is less in sPRR-His group (FIG. 13). Plasma glucose and insulin were increased in DIO mice as compared with the lean control (FIG. 14) indicating that the long-term high fat diet induced type 2 diabetes due to insulin resistance. GTT and ITT were subsequently performed to examine the status of insulin sensitivity. DIO mice exhibited impaired GTT which was almost completely normalized by sPRR-His (FIG. 15A). In parallel, DIO mice had impaired ITT, evidence of insulin resistance. Over the 90 min of the ITT, blood glucose in both DIO and lean control groups gradually came back to the baseline. Strikingly, the DIO+sPRR-His group had much sustained fall in blood glucose following the bolus insulin injection. As reflected from the fall of blood glucose, insulin sensitivity in the DIO+sPRR-His remained at the peak level even at 90 min, contrasting to nearly full recovery of the blood glucose level in the DIO and lean control groups at the last time point (FIG. 15B). DIO mice have pale appearance of the liver (FIG. 16A). After centrifugation of the liver homogenates, the upper white layer reflects the lipid content which was obviously increased in DIO mice as compared with the lean control. This lipid layer was nearly normalized by sPRR-His treatment (FIG. 16B). This result was confirmed by measurement of triglyceride content in the liver (FIG. 16C). The consistent findings from the three different parameters demonstrated a protective role of sPRR-His in treatment of steatosis. Interestingly, sPRR-His infusion didn't affect the circulating triglyceride level (FIG. 17), indicating independence of anti-steatosis effect of sPRR-His on the systemic lipid profile. Tis is an important observation since lipolysis-based anti-obesity therapies would be associated with an adverse consequence of increased circulating lipid levels. Obesity is also a risk factor of chronic kidney disease. The DIO mice had increased urinary albumin excretion, which was attenuated by sPRR-His infusion (FIG. 18).

FIG. 19 shows an effect of sPRR-His on urine volume and apididymal fat mass and in lithium-treated mice. This experiment was originally designed to examine the effect of sPRR-His on lithium-induced diabetes insipidus. LiCl is widely used to treat mental disorder but is associated with polyuria. The mechanism of how LiCl impairs urine concentrating capability is unclear but is likely independent of vasopressin. Male C57/BL6 mice were treated with LiCl alone or in combination with sPRR-His. Although co-administration with sPRR-His did not affect Li-induced polyuria (FIG. 19A) but surprisingly reduced fat mass (FIG. 19B). The image of apididymal fat is shown in FIG. 19C. The fat in the Li+sPRR-His group is smaller and also more "browning" than that in the other two groups. This result suggests that sPRR-His may promote the white to brown conversion of apididymal fat. Regardless of the underlying mechanism, this result suggests a novel therapeutic potential of sPRR in suppressing fat mass although the animals used in this study were not an obesity model. This finding prompted the subsequent investigation of the role of sPRR in diet-induced obesity. In addition, this result indicates that sPRR is primarily effective in attenuating diabetes insipidus due to impairment of vasopressin production or signaling but not that due to lithium toxicity. N=4-5 per group. Data are mean±SE.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Nguyen G (2011) Renin and prorenin receptor in hypertension: What's new? Curr Hypertens Rep 13(1):79-85.
2. Watanabe N, et al. (2012) Soluble (pro)renin receptor and blood pressure during pregnancy: A prospective cohort study. Hypertension 60(5):1250-1256.
3. Nguyen G, et al. (2002) Pivotal role of the renin/prorenin receptor in angiotensin II production and cellular responses to renin. J Clin Invest 109(11):1417-1427.
4. Kinouchi K. et al. (2010) The (pro)renin receptor/ATP6AP2 is essential for vacuolar H+-ATPase assembly in murine cardiomyocytes. Circ Res 107(1):30-34.
5. Cousin C, et al. (2009) Soluble form of the (pro)renin receptor generated by intracellular cleavage by furin is secreted in plasma. Hypertension 53(6):1077-1082.
6. Yoshikawa A. et al. (2011) The (pro)renin receptor is cleaved by ADAM19 in the Golgi leading to its secretion into extracellular space. Hypertens Res 34(5): 599-605.
7. Maruyama N, Segawa T, Kinoshita N, Ichihara A (2013) Novel sandwich ELISA for detecting the human soluble (pro)renin receptor. Front Biosci (Elite Ed) 5: 583-590.
8. Fukushima A, et al. (2013) Increased plasma soluble (pro)renin receptor levels are correlated with renal dysfunction in patients with heart failure. Int J Cardiol 168(4): 4313-4314.
9. Hamada K, et al. (2013) Serum level of soluble (pro)renin receptor is modulated in chronic kidney disease. Clin Exp Nephrol 17(6):848-856.

10. Watanabe N, et al. (2013) Prediction of gestational diabetes mellitus by soluble (pro)renin receptor during the first trimester. J Clin EndocrinolMetab 98(6):2528-2535.
11. Morimoto S, et al. (2014) Serum soluble (pro)renin receptor levels in patients with essential hypertension. Hypertens Res 37(7):642-648.
12. Nguyen G, et al. (2014) Plasma soluble (pro)renin receptor is independent of plasma renin, prorenin, and aldosterone concentrations but is affected by ethnicity. Hypertension 63(2):297-302.
13. Advani A, et al. (2009) The (Pro)renin receptor: Site-specific and functional linkage to the vacuolar H+-ATPase in the kidney. Hypertension 54(2):261-269.
14. Wang F L X, et al. (2016) Antidiuretic action of collecting duct (pro)renin receptor downstream of vasopressin/EP4 receptor. J Am Soc Nephrol, in press.
15. Ramkumar N, et al. (2015) Nephron-specific deletion of the prorenin receptor causes a urine concentration defect. Am J Physiol Renal Physiol 309(1):F48-F56.
16. Berkenstam A, Gustafsson J A (2005) Nuclear receptors and their relevance to diseases related to lipid metabolism. Curr Opin Pharmacol 5(2):171-176.
17. Alberti S, Steffensen K R, Gustafsson J A (2000) Structural characterisation of the mouse nuclear oxysterol receptor genes LXRalpha and LXRbeta. Gene 243(1-2):93-103.
18. Zelcer N, Hong C, Boyadjian R, Tontonoz P (2009) LXR regulates cholesterol uptake through Idol-dependent ubiquitination of the LDL receptor. Science 325(5936): 100-104.
19. Repa J J, Mangelsdorf D J (2000) The role of orphan nuclear receptors in the regulation of cholesterol homeostasis. Annu Rev Cell Dev Biol 16:459-481.
20. Repa J J, et al. (2000) Regulation of absorption and ABC-mediated efflux of cholesterol by RXR heterodimers. Science 289(5484):1524-1529.
21. Caldas Y A, et al. (2011) Liver X receptor-activating ligands modulate renal and intestinal sodium-phosphate transporters. Kidney Int 80(5):535-544.
22. Kittayaruksakul S, Soodvilai S, Asavapanumas N, Muanprasat C, Chatsudthipong V (2012) Liver X receptor activation downregulates organic anion transporter 1 (OAT1) in the renal proximal tubule. Am J Physiol Renal Physiol 302(5):F552-F560.
23. Soodvilai S. Jia Z, Fongsupa S, Chatsudthipong V, Yang T (2012) Liver X receptor agonists decrease ENaC-mediated sodium transport in collecting duct cells. Am J Physiol Renal Physiol 303(12):F1610-F1616.
24. Li W, et al. (2012) Brain-targeted (pro)renin receptor knockdown attenuates angiotensin II-dependent hypertension. Hypertension 59(6):1188-1194.
25. Gonzalez A A, Luffman C, Bourgeois C R, Vio C P, Prieto M C (2013) Angiotensin II-independent upregulation of cyclooxygenase-2 by activation of the (Pro)renin receptor in rat renal inner medullary cells. Hypertension 61(2):443-449.
26. Huang S M, et al. (2009) Tankyrase inhibition stabilizes axin and antagonizes Wnt signalling. Nature 461(7264):614-620.
27. Smith S, Giriat I, Schmitt A. de Lange T (1998) Tankyrase, a poly(ADP-ribose) polymerase at human telomeres. Science 282(5393):1484-1487.
28. Nielsen S, et al. (2002) Aquaporins in the kidney: From molecules to medicine. Physiol Rev 82(1):205-244.
29. Knepper M A, et al. (1996) Renal aquaporins. Kidney Int 49(6):1712-1717.
30. Fujiwara T M, Bichet D G (2005) Molecular biology of hereditary diabetes insipidus. J Am Soc Nephrol 16(10): 2836-2846.
31. Wesche D, Deen P M, Knoers N V (2012) Congenital nephrogenic diabetes insipidus: The current state of affairs. Pediatr Nephrol 27(12):2183-2204.
32. Morello F, et al. (2005) Liver X receptors alpha and beta regulate renin expression in vivo. J Clin Invest 115(7):1913-1922.
33. Gabbi C, et al. (2012) Central diabetes insipidus associated with impaired renal aquaporin-1 expression in mice lacking liver X receptor β. Proc Natl Acad Sci USA 109(8):3030-3034.
34. Tachibana H, et al. (2012) Activation of liver X receptor inhibits osteopontin and ameliorates diabetic nephropathy. J Am Soc Nephrol 23(11):1835-1846.
35. Wang F, et al. (2014) Prostaglandin E-prostanoid4 receptor mediates angiotensin IIinduced (pro)renin receptor expression in the rat renal medulla. Hypertension 64(2):369-377.
36. Jung H J, et al. (2015) Tankyrase-mediated β-catenin activity regulates vasopressininduced AQP2 expression in kidney collecting duct mpkCCDc14 cells. Am J Physiol Renal Physiol 308(5):F473-F486.
37. Cruciat C M, et al. (2010) Requirement of prorenin receptor and vacuolar H+-ATPasemediated acidification for Wnt signaling. Science 327(5964):459-463.
38. Oshima Y, Morimoto S, Ichihara A (2014) Roles of the (pro)renin receptor in the kidney. World J Nephrol 3(4):302-307.
39. Rousselle A, Sihn G, Rotteveel M, Bader M (2014) (Pro)renin receptor and V-ATPase: From Drosophila to humans. Clin Sci (Lond) 126(8):529-536.
40. Krop M, Lu X, Danser A H, Meima M E (2013) The (pro)renin receptor. A decade of research: What have we learned? Pflugers Arch 465(1):87-97.
41. Song R, Preston G, Ichihara A, Yosypiv I V (2013) Deletion of the prorenin receptor from the ureteric bud causes renal hypodysplasia. PLoS One 8(5):e63835.
42. Yasui M, Zelenin S M, Celsi G. Aperia A (1997) Adenylate cyclase-coupled vasopressin receptor activates AQP2 promoter via a dual effect on CRE and AP1 elements. Am J Physiol 272(4 Pt 2):F443-F450.
43. Zharkikh L, et al. (2002) Renal principal cell-specific expression of green fluorescent protein in transgenic mice. Am J Physiol Renal Physiol 283(6):F1351-F1364.
44. Lu X, et al. (2015) Activation of ENaC in collecting duct cells by prorenin and its receptor PRR: Involvement of Nox4-derived hydrogen peroxide. Am J Physiol Renal Physiol, 10.1152/ajprenal.00492.2015.
45. Kim R J, Malattia C, Allen M, Moshang T, Jr, Maghnie M (2004) Vasopressin and desmopressin in central diabetes insipidus: adverse effects and clinical considerations. Pediatr Endocrinol Rev 2(Suppl 1):115-123.
46. Granger J P, West D, Scott J (1994) Abnormal pressure natriuresis in the dog model of obesity-induced hypertension. Hypertension 23(1, Suppl):18-111.
47. West D B, Wehberg K E, Kieswetter K. Granger J P (1992) Blunted natriuretic response to an acute sodium load in obese hypertensive dogs. Hypertension 19(1, Suppl):I96-I100.
48. Spark R F, Arky R A, Boulter P R, Saudek C D, O'Brian J T (1975) Renin, aldosterone and glucagon in the natriuresis of fasting. N Engl J Med 292(25):1335-1340.
49. Weinsier R L (1971) Fasting—a review with emphasis on the electrolytes. Am J Med 50(2):233-240.

50. Zhang H. et al. (2005) Collecting duct-specific deletion of peroxisome proliferatoractivated receptor gamma blocks thiazolidinedione-induced fluid retention. Proc Natl Acad Sci USA 102(26):9406-9411.
51. Guan Y, et al. (2005) Thiazolidinediones expand body fluid volume through PPARgamma stimulation of ENaC-mediated renal salt absorption. Nat Med 11(8):861-866.
52. Kuipers I, et al. (2010) Activation of liver X receptor-alpha reduces activation of the renal and cardiac renin-angiotensin-aldosterone system. Laboratory Investigation 90(4):630-636.
53. Wang F. et al. (2015) Renal medullary (pro)renin receptor contributes to angiotensin II-induced hypertension in rats via activation of the local renin-angiotensin system. BMC Med 13:278.
54. Nguyen, G, Delarue, F, Burckle, C, Bouzhir, L. Giller, T, Sraer, J D: Pivotal role of the renin/prorenin receptor in angiotensin II production and cellular responses to renin. *J Clin Invest*, 109: 1417-1427, 2002.
55. Cousin, C, Bracquart, D, Contrepas, A, Corvol, P, Muller, L, Nguyen, G: Soluble form of the (pro)renin receptor generated by intracellular cleavage by furin is secreted in plasma. *Hypertension*, 53: 1077-1082, 2009.
56. Watanabe, N, Bokuda, K, Fujiwara, T, Suzuki, T. Mito, A, Morimoto, S, Jwa, S C, Egawa, M. Arai, Y, Suzuki, F, Sago, H. Ichihara, A: Soluble (pro)renin receptor and blood pressure during pregnancy: a prospective cohort study. *Hypertension*. 60: 1250-1256, 2012.
57. Watanabe, N, Morimoto, S, Fujiwara, T, Suzuki, T. Taniguchi, K, Mori, F. Ando, T, Watanabe, D, Kimura. T, Sago, H, Ichihara, A: Prediction of gestational diabetes mellitus by soluble (pro)renin receptor during the first trimester. *The Journal of clinical endocrinology and metabolism*. 98: 2528-2535, 2013.
58. Fukushima, A. Kinugawa, S, Homma, T, Masaki, Y, Furihata, T, Abe, T, Suga, T, Takada, S, Kadoguchi, T, Okita, K, Matsushima, S, Tsutsui, H: Increased plasma soluble (pro)renin receptor levels are correlated with renal dysfunction in patients with heart failure. *International journal of cardiology,* 168: 4313-4314, 2013.
59. Bonakdaran, S. Azami, G, Tara, F, Poorali, L: Soluble (Pro) Renin Receptor is a predictor of gestational diabetes mellitus. *Current diabetes reviews,* 2016.
60. Nishijima, T, Tajima, K. Yamashiro, Y, Hosokawa, K. Suwabe, A, Takahashi, K. Sakurai, S: Elevated Plasma Levels of Soluble (Pro)Renin Receptor in Patients with Obstructive Sleep Apnea Syndrome in Parallel with the Disease Severity. *The Tohoku journal of experimental medicine,* 238: 325-338, 2016.
61. Kreienbring, K, Franz, A, Richter, R, Dragun, D, Heidecke, H, Dechend, R, Muller, D N, Sehouli, J, Braicu, E I: Predictive and Prognostic Value of sPRR in Patients with Primary Epithelial Ovarian Cancer. *Analytical cellular pathology.* 2016: 6845213, 2016.
62. Lu, X, Wang, F, Xu, C, Soodvilai, S, Peng, K, Su, J, Zhao, L, Yang, K T, Feng, Y, Zhou, S F, Gustafsson, J A, Yang, T: Soluble (pro)renin receptor via beta-catenin enhances urine concentration capability as a target of liver X receptor. *Proc Natl Acad Sci USA,* 113: E1898-1906, 2016.

I claim:

1. A method of treating a fluid and electrolyte disorder comprising administering an effective amount of soluble (pro)renin receptor (sPRR) to a subject diagnosed with a fluid and electrolyte disorder.

2. The method of claim 1, wherein the fluid and electrolyte is central diabetes insipidus (CDI), nephrogenic diabetes insipidus (NDI), hemorrhagic shock, septic shock, or plasma volume contraction due to a variety of etiologies.

3. The method of claim 1 further comprising the step of testing the subject to determine whether the subject has a fluid and electrolyte disorder prior to administering the sPRR.

4. The method of claim 1, wherein administering an effective amount of sPRR comprises administering a vehicle carrying an effective amount of sPRR.

5. The method of claim 4, wherein the vehicle is a nanoparticle.

6. The method of claim 5, wherein the nanoparticle is a lipsome or polymer.

7. The method of claim 1, wherein the sPRR is a fusion protein.

8. The method of claim 1 further comprising administering a known therapeutic.

9. The method of claim 8, wherein the known therapeutic is known to treat a fluid and electrolyte disorder.

10. The method of claim 8, wherein the known therapeutic is known to reduce body weight.

11. The method of claim 1, wherein the sPRR is wild type sPRR.

12. The method of claim 1, wherein sPRR is 70-99% identical to wild type sPRR.

13. The method of claim 1, wherein the sPRR is administered in an amount of 10-300 µg/kg/day.

* * * * *

SEQUENCE LISTING

```
<160> NUMBER OF SEQ ID NOS: 1

<210> SEQ ID NO 1
<211> LENGTH: 258
<212> TYPE: PRT
<213> ORGANISM: Homo sapiens

<400> SEQUENCE: 1

Ala Asn Glu Phe Ser Ile Leu Arg Ser Pro Gly Ser Val Val Phe Arg
1               5                   10                  15

Asn Gly Asn Trp Pro Ile Pro Gly Asp Arg Ile Pro Asp Val Ala Ala
            20                  25                  30

Leu Ser Met Gly Phe Ser Val Lys Glu Asp Leu Ser Trp Pro Gly Leu
        35                  40                  45

Ala Val Gly Asn Leu Phe His Arg Pro Arg Ala Thr Ile Met Val Thr
    50                  55                  60

Val Lys Gly Val Asp Lys Leu Ala Leu Pro Thr Gly Ser Val Ile Ser
65                  70                  75                  80

Tyr Pro Leu Glu Asn Ala Val Pro Phe Ser Leu Asp Ser Val Ala Asn
                85                  90                  95

Ser Ile His Ser Leu Phe Ser Glu Glu Thr Pro Val Val Leu Gln Leu
            100                 105                 110

Ala Pro Ser Glu Glu Arg Val Tyr Met Val Gly Lys Ala Asn Ser Val
        115                 120                 125

Phe Glu Asp Leu Ser Val Thr Leu Arg Gln Leu Arg Asn Arg Leu Phe
    130                 135                 140

Gln Glu Asn Ser Val Leu Asn Ser Leu Pro Leu Asn Ser Leu Ser Arg
145                 150                 155                 160

Asn Asn Glu Val Asp Leu Leu Phe Leu Ser Glu Leu Gln Val Leu His
```

-continued

```
                165                 170                 175
Asp Ile Ser Ser Leu Leu Ser Arg His Lys His Leu Ala Lys Asp His
            180                 185                 190

Ser Pro Asp Leu Tyr Ser Leu Glu Leu Ala Gly Leu Asp Glu Leu Gly
        195                 200                 205

Lys Arg Tyr Gly Glu Asp Ser Glu Gln Phe Arg Asp Ala Ser Arg Ile
    210                 215                 220

Leu Val Asp Ala Leu Gln Lys Phe Ala Asp Asp Met Tyr Ser Leu Tyr
225                 230                 235                 240

Gly Gly Asn Ala Val Val Glu Leu Val Thr Val Lys Ser Phe Asp Thr
            245                 250                 255

Ser Leu
```